(12) United States Patent
Cuiffi et al.

(10) Patent No.: US 10,913,925 B2
(45) Date of Patent: Feb. 9, 2021

(54) MODULAR PLATFORM FOR TISSUE INTEGRATED CELL CULTURE

(71) Applicants: The Charles Stark Draper Laboratory, Inc., Cambridge, MA (US); The Massachusetts Institute of Technology, Cambridge, MA (US)

(72) Inventors: Joseph Cuiffi, Fort Myers, FL (US); Jeffrey T. Borenstein, Newton, MA (US); Anilkumar Harapanahalli Achyuta, Tampa, FL (US); Mark J. Mescher, West Newton, MA (US); Linda Griffith, Cambridge, MA (US); Samuel Walker Inman, Boston, MA (US)

(73) Assignees: The Charles Stark Draper Laboratory, Inc., Cambridge, MA (US); The Massachusetts Institute of Technology, Cambridge, MA (US)

( * ) Notice: Subject to any disclaimer, the term of this patent is extended or adjusted under 35 U.S.C. 154(b) by 372 days.

(21) Appl. No.: 15/360,457

(22) Filed: Nov. 23, 2016

(65) Prior Publication Data

US 2017/0137768 A1 May 18, 2017

Related U.S. Application Data

(62) Division of application No. 13/951,067, filed on Jul. 25, 2013, now Pat. No. 9,528,082.

(Continued)

(51) Int. Cl.
*C12M 3/00* (2006.01)
*C12M 1/00* (2006.01)
(Continued)

(52) U.S. Cl.
CPC ............ *C12M 23/44* (2013.01); *C12M 21/08* (2013.01); *C12M 23/12* (2013.01); *C12M 23/42* (2013.01);
(Continued)

(58) Field of Classification Search
CPC .............................. C12M 23/44; C12M 21/08
See application file for complete search history.

(56) References Cited

U.S. PATENT DOCUMENTS 7,445,926 B2   11/2008  Mathies et al.
8,318,479 B2   11/2012  Domansky et al.
(Continued)

FOREIGN PATENT DOCUMENTS

EP    0823483 A1    2/1998
EP    1932904 A2    6/2008
(Continued)

OTHER PUBLICATIONS

Grover, William, et al., "Monolithic membrane valves and diaphragm pumps for practical large-scale integration into glass microfluidic devices", Sensors and Actuators B 89 (2003) pp. 315-323.
(Continued)

*Primary Examiner* — Nathan A Bowers
(74) *Attorney, Agent, or Firm* — Hamilton, Brook, Smith & Reynolds, P.C.

(57) ABSTRACT

The systems and methods disclosed herein are generally related to a cell culture system. More particularly, the systems and methods enable the culturing and interconnecting of a plurality of tissue types in a biomimetic environment. By culturing organ specific tissue types within a biomimetic environment and interconnecting each of the organ systems in a physiologically meaningful way, experiments can be conducted on in vitro cells that substantially mimic the responses of in vivo cell populations. In some
(Continued)

implementations, the system is used to monitor how organ systems respond to agents such as toxins or medications. The system enables the precise and controlled delivery of these agents, which, in some implementations, enables the biomimetic dosing of drugs in humans to be mimicked.

15 Claims, 13 Drawing Sheets

Related U.S. Application Data

(60) Provisional application No. 61/675,688, filed on Jul. 25, 2012.

(51) Int. Cl.
| | | |
|---|---|---|
| *C12M 1/32* | (2006.01) | |
| *C12M 1/34* | (2006.01) | |
| *C12M 1/36* | (2006.01) | |
| *G01N 33/50* | (2006.01) | |

(52) U.S. Cl.
CPC ............ *C12M 23/48* (2013.01); *C12M 23/58* (2013.01); *C12M 29/00* (2013.01); *C12M 41/00* (2013.01); *C12M 41/44* (2013.01); *C12M 41/48* (2013.01); *G01N 33/5008* (2013.01)

(56) References Cited

U.S. PATENT DOCUMENTS

| | | | |
|---|---|---|---|
| 9,249,387 B2 | 2/2016 | Cuiffi et al. | |
| 9,528,082 B2 | 12/2016 | Cuiffi et al. | |
| 9,777,252 B2 | 10/2017 | Cuiffi et al. | |
| 2003/0215941 A1* | 11/2003 | Campbell | B82Y 30/00 435/325 |
| 2005/0255003 A1* | 11/2005 | Summersgill | B01F 5/0646 422/606 |
| 2005/0260745 A1 | 11/2005 | Domansky et al. | |
| 2006/0110822 A1* | 5/2006 | Robbins | C12M 23/12 435/289.1 |
| 2006/0199260 A1 | 9/2006 | Zhang et al. | |
| 2006/0281143 A1 | 12/2006 | Liu et al. | |
| 2009/0305397 A1 | 12/2009 | Dodgson et al. | |
| 2010/0165784 A1 | 7/2010 | Jovanovich et al. | |
| 2010/0303687 A1 | 12/2010 | Blaga et al. | |
| 2011/0039303 A1 | 2/2011 | Jovanovich et al. | |
| 2012/0183987 A1* | 7/2012 | Gevaert | C12N 5/0693 435/29 |
| 2012/0214189 A1 | 8/2012 | Shuler et al. | |
| 2014/0030752 A1 | 1/2014 | Cuiffi et al. | |
| 2014/0212964 A1 | 7/2014 | Cuiffi et al. | |
| 2016/0145553 A1 | 5/2016 | Cuiffi et al. | |

FOREIGN PATENT DOCUMENTS

| | | |
|---|---|---|
| WO | 1997004074 A1 | 2/1997 |
| WO | 2007021343 A2 | 2/2007 |
| WO | 2011014674 A2 | 2/2011 |
| WO | WO 2014/018770 | 1/2014 |
| WO | WO 2014/120772 | 8/2014 |

OTHER PUBLICATIONS

Gu, Wei, et al., "Computerized microfluidic cell culture using elastomeric channels and Braille displays", PNAS, Nov. 9, 2004, vol. 101, No. 45, pp. 15861-15866.
International Search Report and Written Opinion for PCT/US2013/052089 dated Oct. 31, 2013.
International Search Report and Written Opinion for PCT/US2014/013604 dated May 20, 2014.
International Preliminary Report on Patentability PCT/US2013/052089 dated Feb. 5, 2015.
International Preliminary Report on Patentability for PCT/US2014/013604 dated Aug. 13, 2015.
U.S. Office Action in U.S. Appl. No. 14/167,590 dated Jun. 11, 2015.
U.S. Notice of Allowance in U.S. Appl. No. 14/167,590 dated Sep. 22, 2015.
U.S. Office Action in U.S. Appl. No. 13/951,067 dated Mar. 20, 2015.
U.S. Office Action in U.S. Appl. No. 13/951,067 dated Jul. 8, 2015.
U.S. Office Action in U.S. Appl. No. 13/951,067 dated Mar. 31, 2016.
U.S. Notice of Allowance in U.S. Appl. No. 13/951,067 dated Aug. 15, 2016.
U.S. Office Action in U.S. Appl. No. 15/012,577 dated Apr. 10, 2017.
Zhang, Chi, et al., "Towards a human-on-chip: Culturing multiple cell types on a chip with compartmentalized microenvironments", Lab on a Chip, vol. 9, No. 22, Nov. 21, 2009, pp. 3165-3312.
Notice of Allowance in U.S. Appl. No. 15/012,577, filed Feb. 1, 2016, entitled: Modular Platform for Multi-Tissue Integrated Cell Culture, dated Jul. 21, 2017.

* cited by examiner

MODULAR PLATFORM FOR TISSUE INTEGRATED CELL CULTURE

CROSS-REFERENCE TO RELATED PATENT APPLICATIONS

This application is a divisional of, and claims priority to, U.S. patent application Ser. No. 13/951,067 filed Jul. 25, 2013, which claims priority to U.S. Provisional Patent Application No. 61/675,688, filed Jul. 25, 2012, both of which are incorporated herein by reference in their entirety.

BACKGROUND OF THE DISCLOSURE

In vitro models of human tissue are typically cultured as single cultures in isolated environments. The isolation of the tissue cultures removes the interplay between the tissue cultures that is present in in vivo systems. The isolated tissue environments make it difficult to study systemic issues, such as drug dosing, in in vitro cultures.

SUMMARY OF THE DISCLOSURE

According to one aspect of the disclosure, a modular device for culturing cells includes a control plate, a first and a second cell culture vessel, and an actuator. The first and second cell culture vessels are reversibly coupled to the control plate and are also respectively configured to culture a first type of cells and a second type of cells. The actuator is within the control plate and configures a fluid flow between the first and second cell culture vessels.

In some implementations, the control plate defines a first set of channels to route the fluid flow to at least one of the first and second cell culture vessels. In certain implementations, the cell culturing device also includes a fluid routing plate, which is configured to reversibly receive the first and second cell culture vessels. The fluid routing plate is also configured to couple the first and second cell culture vessels to the control plate. The fluid routing plate defines a second set of channels to route the fluid flow from the control plate to the first and/or second cell culture vessel.

In some implementations, the first and second cell culture vessels each include a fluid inlet port and a fluid outlet port to reversibly and fluidically couple to respective channels in the fluid routing plate. In yet other implementations, the actuator is configured to control a valve within the fluid routing plate. The actuator controls at least one of the route and flow rate of the fluid flow through the fluid routing plate. In certain implementations, the actuator is configured to close the valve by deforming a control membrane within the valve.

In some implementations, the actuator is configured to introduce or withdraw a predetermined amount of an agent, such as a medication or a toxin, into the fluid flow between the first and second cell culture vessels. In some implementations, the first type of cells corresponds to a first organ system and the second type of cells corresponds to a second organ system. The organ systems are one or a kidney, a lung, and a liver. In some implementations, the first and second organ systems are different.

In some implementations, the actuator is one of a pneumatic actuator, an electro-mechanical actuator, and a valve. In certain implementations, the control plate includes a plurality of sensors to measure a parameter in the first and second cell culture vessels.

In some implementations, the first and second cell culture vessels are disposable and the control plate is configured to withstand a sterilization process. In yet other implementations, the first and second cell culture vessels each include a membrane to support a plurality of cells.

According to another aspect of the disclosure, a method for culturing a plurality of cells includes providing a first cell culture vessel configured to culture a first cell type, providing a second cell culture vessel configured to culture a second cell type, and providing a control plate. The control plate is configured to reversibly couple to the first and second cell culture vessels and to also control a first fluid flow between the first and second cell culture vessels.

In some implementations, the method also includes disposing a first plurality of cells of the first cell type into the first cell culture vessel and disposing a second plurality of cells of the second cell type into the second cell culture vessel. In some implementations, the method further includes coupling the first and second cell culture vessels to the control plate, and then flowing the fluid between the first cell culture vessel and the second cell culture vessel along the first fluid path.

In yet other implementations, the method includes reversibly coupling a third cell culture vessel, which is configured to culture a third type of cell, to the control plate. In some of these implementations, the method also includes activating an actuator coupled to the control plate to form a second fluid path to the third cell culture vessel.

In some implementations, the first fluid flow includes a liquid flow and the second fluid flow includes a gas flow. In certain implementations, the first fluid path couples the first cell culture vessel to the second cell culture vessel and the second fluid path couples the second cell culture vessel to the third cell culture vessel.

In some implementations, prior to coupling the third cell culture vessel to the control plate, the method includes decoupling at least one of the first and second cell culture vessels from the control plate and modifying the first fluid path.

In yet other implementations, the method includes setting a state of an actuator incorporated into the control plate to control at least one of the route and flow rate of the fluid flow between the first cell culture vessel and the second cell culture vessel. In some implementations, the method includes injecting or withdrawing, by an actuator, a predetermined amount of an agent, such as a medication or a toxin, into at least one of the first cell culture vessel and the second cell culture vessel.

In certain implementations, the first cell type corresponds to a first organ system and the second cell type corresponds to second organ system. In some implementations, the organ systems correspond to one of a liver, a kidney, and a lung, and, in certain implementations, the first and second organ systems are different.

In some implementations, the method includes measuring at least one parameter within the first and/or second cell culture vessel. In some implementations, an agent is delivered into at least one of the first cell culture vessel and the second cell culture vessel and then a response to the agent is measured.

According to yet another aspect of the disclosure, a system for culturing cells includes a disposable fluid routing plate. The fluid routing plate includes a plurality of fluid channels and at last two receptacles configured for removably accepting respective first and second cell culture vessels. The at least two receptacles are also configured to couple the first and second cell culture vessels to respective channels of the plurality of fluid channels. The fluid routing plate also includes at least one valve coupled to at least two of the fluid channels. The at least one valve is configured to control a path of a fluid flow through the plurality of fluid channels and form a fluid path between the at least two receptacles. The system also includes a reusable control plate configured for coupling to the fluid routing plate. The control plate also includes an actuator for controlling the valve in the fluid routing plate.

In some implementations, the system also includes a computer processor coupled to the control plate and configured to output control signals to the control plate to configure the position of the actuator. In some implementations, the system also includes a sensor for measuring a parameter of a cell culture disposed in one of the first and second cell culture vessels. In other implementations, the system includes a computer processor coupled to the sensor and configured to receive data from the sensor.

In yet other implementations, the system includes a fluid pump coupled to one of the control plate and the fluid routing plate to generate a fluid flow along the fluid path between the at least two receptacles. In some implementations, at least one of the receptacles is configured to receive a plurality of types of modular cell culture vessels configured for culturing different respective cell types. In certain implementations, the system also includes an actuator configured to inject or withdraw a predetermined amount of an agent, such as a medication or a toxin, into the plurality of fluid channels.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The systems and methods disclosed are generally related to a cell culture system. More particularly, the systems and methods enable culturing and interconnecting a plurality of tissue types in a biomimetic environment. By culturing organ specific tissue types within a biomimetic environment and interconnecting each of the organ systems in a physiologically meaningful way, experiments can be conducted on in vitro cells that substantially mimic the responses of in vivo cell populations. In some implementations, the system is used to monitor how organ systems respond to agents such as toxins or medications. The system enables the precise and controlled delivery of these agents, which, in some implementations, allows the biomimetic dosing of drugs in humans to be mimicked.

Figure 1:
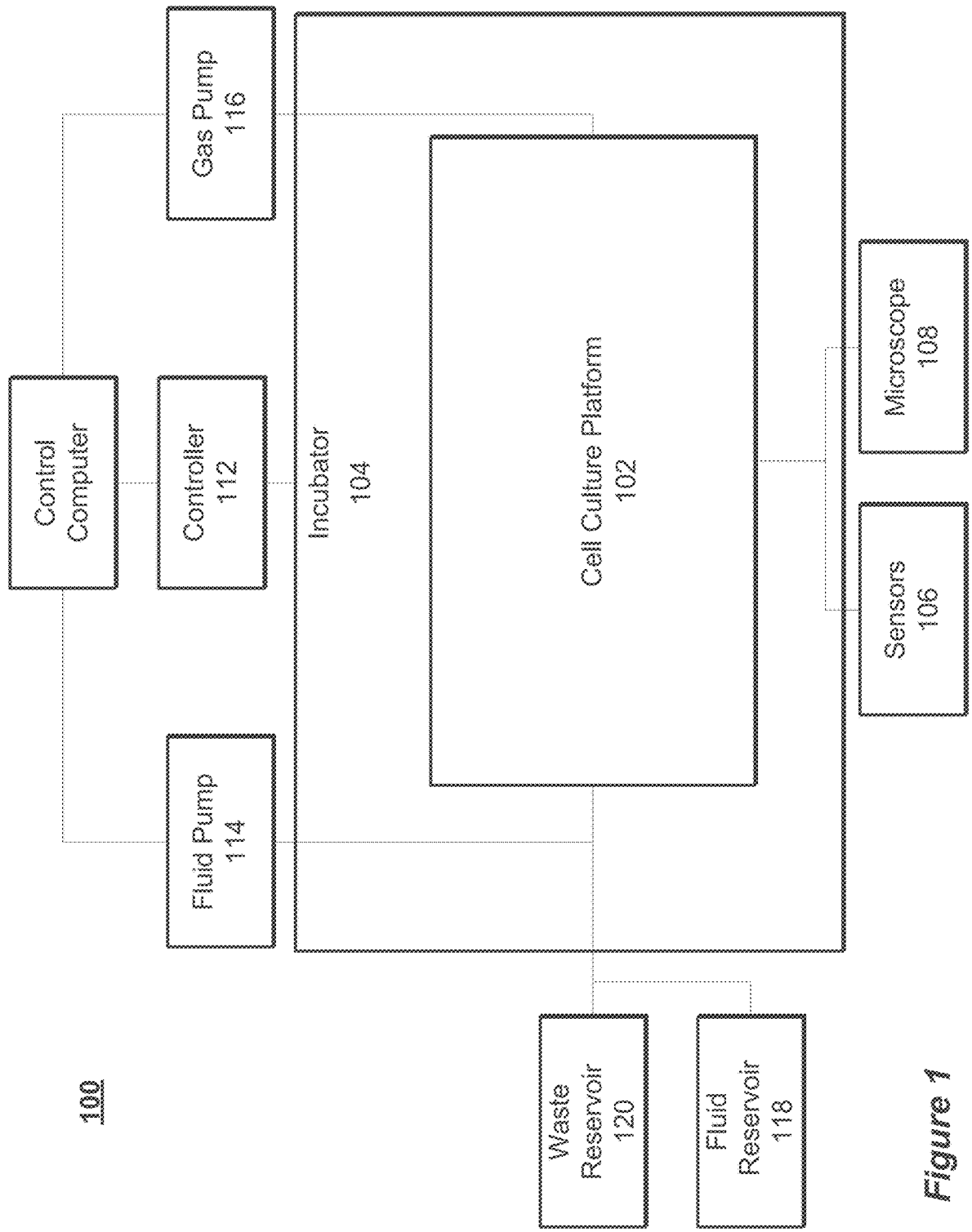
FIG. 1 is a schematic of a cell culture system.

FIG. 1 illustrates a cell culture system 100. The cell culture system 100 includes a cell culture platform 102 within an incubator 104. The cell culture system 100 also includes a plurality of sensors 106 and a microscope 108 to monitor the cells within the cell culture platform 102. A control computer 110 uses a controller 112 to control the flow of fluids and gases through the cell culture platform 102. The fluid flow and gas flow is caused by at least one fluid pump 114 and at least one gas pump 116, respectively. Prior to flowing through the cell culture platform 102, fluid is stored in a fluid reservoir 118 and responsive to flowing through the cell culture platform 102 the fluid is stored in a waste reservoir 120.

As described above, the cell culture system 100 includes a cell culture platform 102. The cell culture platform 102 and its components are described further in relation to FIGS. 2-9, but briefly, the cell culture platform 102 is a modular platform for culturing cells and/or tissue. As discussed below, the cell culture platform 102 includes a control plate, a fluid flow plate and a plurality of cell culture vessels. In some implementations, the control plate is reusable and includes actuators, valves and sensors used in the culture and monitoring of cells. In some implementations, the fluid flow plate and/or the cell culture vessels are disposable.

The cell culture platform 102 is housed within an incubator 104. The incubator 104 maintains an environment within the cell culture platform 102 that is conducive for the culturing of the cells and/or tissue. In some implementations, the incubator 104 controls and/or maintains a predetermined temperature, humidity, carbon dioxide level, oxygen level, or any combination thereof. For example, the incubator 104 may be configurable to maintain conditions within the cell culture platform 102 that mimic conditions within the human respiratory system. In another example, the incubator 104 is configured to maintain standard cell culture environments, as outlined by a cell culture protocol.

For example, the incubator 104 can maintain a temperature between about 32° C. and about 37° C. with humidity between about 50% and about 100%. In some implementations, the incubator 104 removes off gases generated by the cells within the cell culture platform 102. The incubator 104 also includes a plurality of access ports (not illustrated). The ports allow sensor connections, flow lines, and other lines to pass from the outside environment to the interior of the incubator 104 without affecting the controlled environment within the incubator 104.

In some of these implementations, the cell culture system 100 does not include a standalone incubator 104. In those implementations, the cell culture vessels of the cell culture platform 102 are reversibly sealed and include heating and other elements that maintain an appropriate environmental condition within each cell culture vessel.

The cell culture system 100 also includes a plurality of sensors 106. In some implementations, one or more of the sensors 106 described herein are housed within (or a component of) the cell culture platform 102. A further description of the sensors 106, including their use and placement, is described below. In brief, the sensors 106 can be used to monitor one or more parameters within the cell culture platform 102. For example, the sensors 106 can monitor biomarkers, flow rates, pressures, temperatures, gas compositions (e.g., oxygen and carbon dioxide levels), chemical compositions (e.g., drug, toxin and metabolite concentrations), pH levels, electrical parameters (e.g., trans-epithelial electrical resistance) or any combination thereof. In some implementations, the sensors are used for feedback by the control computer 110 in controlling system parameters (e.g, environmental conditions) within the cell culture platform 102 and/or incubator 104.

Also as illustrated in FIG. 1, the cell culture system 100 includes a microscope 108. In some implementations, at least a portion of the cell culture platform 102 is configured to allow visual inspectional of the cells and/or tissue within the cell culture platform 102. For example, the components of the cell culture platform 102 are manufactured from substantially clear materials and/or include view ports. The microscope 108 is used to view cells and/or tissue cultured in the cell culture platform 102. In some implementations, the microscope 108 is configured to record still or moving images of the cells and/or tissue within the cell culture platform 102. In some implementations, the microscope 108 is an optical light microscope, confocal microscope, fluorescent microscope, or, in general, any type of microscope used in the field of cellular imaging and analysis.

The cell culture system 100 further includes a control computer 110 and a controller 112. In general the control computer 110 controls the components described herein of the cell culture system 100. In some implementations, the control computer 110 is a general purpose computing device. For example, the control computer 110 can be a laptop, tablet computer, or smartphone. In other implementations, the control computer 110 is a special purposed computer device and includes one or more processors and at least one computer readable medium, such as a hard drive, compact discs, or other storage device. Processor executable instructions are stored on the computer readable medium. When executed, the instructions cause the control computer 110 to perform the functions and methods described herein. For example, the control computer 110 controls the flow of a fluid into and out of the cell culture platform 102 by controlling fluid pumps 114. As described above, in some implementations the control computer 110 receives data from the plurality of sensors 106 and maintains system conditions responsive to the received data. The control computer 110 stores the sensor and other data on the computer readable medium in response to a request from a user. In some implementations, the control computer 110 enables a user to set specific system parameters through a user interface.

The control computer 110 interfaces with the other components of the cell culture system 100 through a controller 112. In some implementations, the controller 112 is a component of the control computer 110 or the cell culture platform 102, and is implemented as hardware and/or software. In other implementations, the controller 112 is a standalone device that interfaces with the control computer 110 and various components of the cell culture system 100 through USB, Firewire, or a similar connection.

The controller includes a plurality of inputs and a plurality of outputs through which it interfaces with the various components of the cell culture system 100. The plurality of inputs and outputs of the controller 112 can be digital and/or analog inputs and outputs. In some implementations, the controller 112 includes at least one processor. Using the at least one processor, the controller 112 preprocesses inputs prior to transmitting the input to the control computer 112. For example, the controller 112 may "pre-filter" or compress sensor data before transmitting the sensor data to the control computer 110. In yet other implementations, instructions are loaded onto the controller 112 such that the controller 112 can control the cell culture system 100 without instruction from the control computer 110. In some implementations, the controller 112 and/or computer 110 alert a user when the cell culture system 100 behavior deviates from predetermined ranges. For example, the control computer 110 may send an alert to the user when the control computer 110 detects a temperature drop in the incubator 104.

Referring again to FIG. 1, the cell culture system 100 includes at least one fluid pump 114 and at least one gas pump 116. The fluid pump 114 and the gas pump 116 (collectively referred to simply as pumps) flow liquids and/or gases into and through the cell culture platform 102. Extra fluid is stored within the fluid reservoir 118 and can be deposited into a waste reservoir after flowing through the cell culture platform 102. In other implementations, the fluid is recirculated through the cell culture platform 102. As illustrated, the pumps are independent from the cell culture platform 102. As described below, in some implementations, the pumps are housed within the cell culture platform 102. The pumps can include peristaltic pumps, syringe pumps, a series of actuators (i.e., pneumatic pumps), or any combination thereof. In some implementations the pumps are configured to produce a smooth flow, pulsatile flow, periodic flow, or any combination thereof through the cell culture platform 102. In yet other implementations, the pumps are directional and can serve as one way valves within the cell culture platform 102. For example, one way pumps can be included within the cell culture platform 102 to force flow in a predetermined manner and not allow backflow during a pulsatile flow.

The foregoing pumps flow a fluid through the cell culture platform 102 and into the below described cell culture vessels. Example fluids include growth medium (or other fluids for cellular growth and sustenance), test agents, toxins, medicaments (e.g., antibiotics, vaccines, biologics, and medical countermeasures), or any combination thereof. In some implementations, the pumps are configured to induce a predetermined shear force on the cells within the cell culture platform 102. The shear force may be selected to mimic physiological conditions or for experimental purposes. For example, epithelial cells may form more physiologically representative cellular barriers when cultured under an appropriate shear force. In some implementations, the flow rates at which the pumps flow fluid are selected to mimic blood flow rates typically seen in parts of the circularity system.

Figure 2:
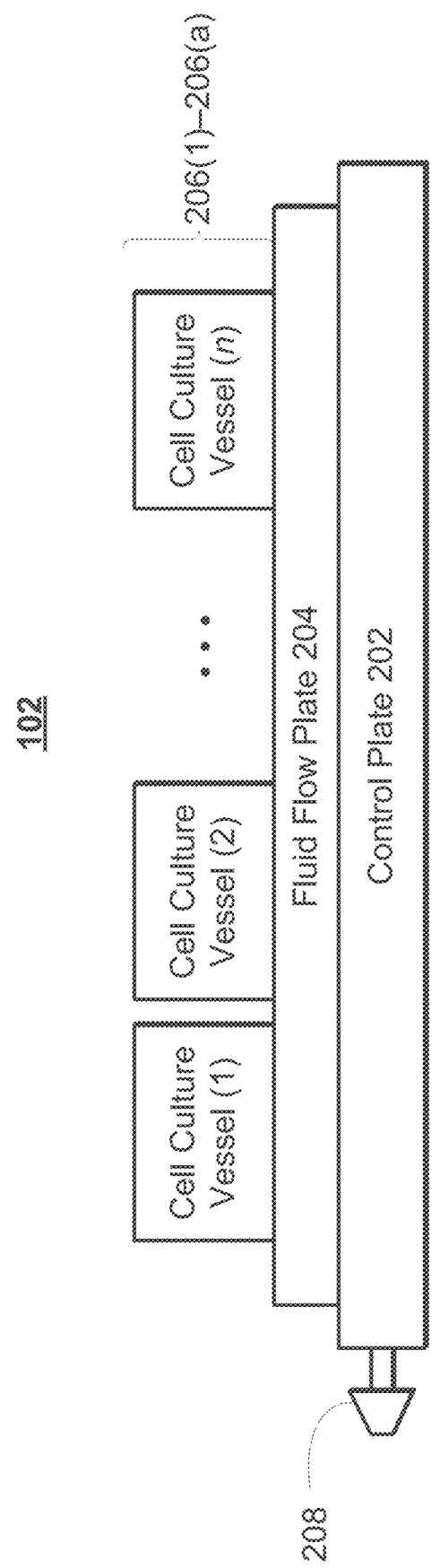
FIG. 2 illustrates a schematic of an example cell culture platform that can be used in the cell culture system of FIG. 1.

Referring now to FIG. 2, FIG. 2 is a schematic illustrating components of the cell culture platform 102. The individual components of the cell culture platform 102 are described in detail in relation to FIGS. 4-9. As a brief introduction, the cell culture platform 102 includes a control plate 202, a fluid flow plate 204, and a plurality of cell culture vessels 206(1)-(n). The fluid flow plate 204 is coupled to the control plate 202, and a plurality of cell culture vessels 206(1)-206(n) are coupled atop the fluid flow plate 204. The cell culture platform 102 further includes a plurality of fluid and/or gas inlet/outlet ports 208. As illustrated, the ports 208 are components of the control plate 202. In other implementations, the control plate 202, fluid flow plate 204, and/or cell culture vessels 206(1)-206(n) each include one or more ports 208.

Continuing the cell culture platform 102 overview, the cell culture platform 102 is used to culture cells and/or tissues. In some implementations, this includes the culture of multiple types of cells and/or tissue from different organ systems. In some implementations, as described below, the cell culture vessels 206 are configured to include 3-dimensional cell culture scaffolds to support and culture the cells and/or tissues. The remaining plates of the cell culture platform 102 facilitate interaction (e.g, fluidic communication) between the cells/tissues cultured within the cell culture vessels 206(1)-206(n), and enable the cell culture vessels 206 to be interconnected in physiologically meaningful ways.

In some implementations, the components of the cell culture platform 102 are reversibly coupled to one another. For example, the components of the cell culture platform 102 can be coupled to one another with claps, screws, via vacuum, adhesive or any combination thereof. In some implementations, the coupling element (e.g, a screw) that is used to couple the cell culture vessel 206 to the fluid flow plate 204 passes through the fluid flow plate 204 to also couple the fluid flow plate 204 to the control plate 202.

In certain implementations, one or more of the components of the cell culture platform 102 are disposable and/or reusable. For example, the control plate 202 may house control connections to the controller 112, sensor connections, actuators, custom components, or any combination thereof is intended to be reused with disposable fluid flow plates 204 and disposable cell culture vessels 206.

In some implementations, the disposable elements include passive structures that are produced using low-cost processes such as machining, injection modling, or embossing. In some implementations, these passive structures are controlled via actuators within the control plate 202. In some implementations, the control plate 202 provides a foundation to which disposable fluid flow plates 204 and cell culture vessels 206 may be modularly added.

Figure 3A:
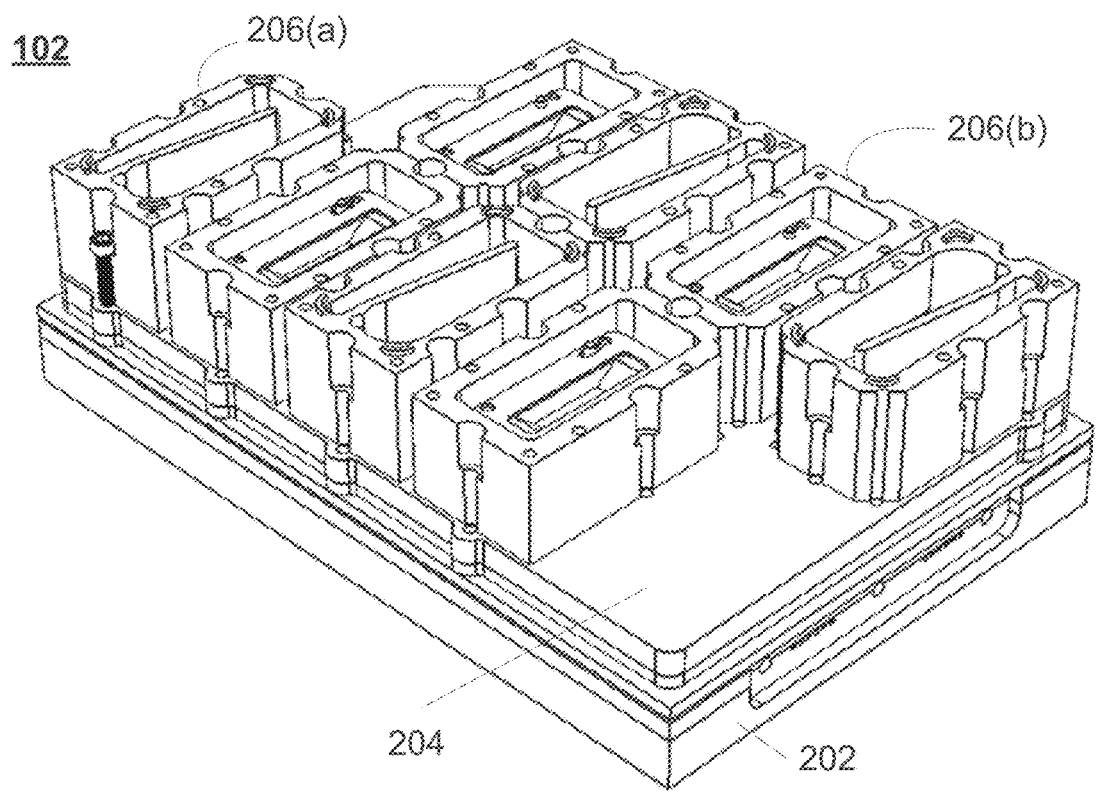
FIGS. 3A and 3B illustrate solid models of an example cell culture platform that can be used in the cell culture system of FIG. 1.

FIG. 3A is solid model illustrating cell culture platform 102 in greater detail. As illustrated, eight cell culture vessels 206 are coupled to a fluid flow plate 204, which is, in turn, coupled to a control plate 202. The control plate 202 includes a first type of cell culture vessel 206(a) and a second type of cell culture vessel 206(b).

Figure 3B:
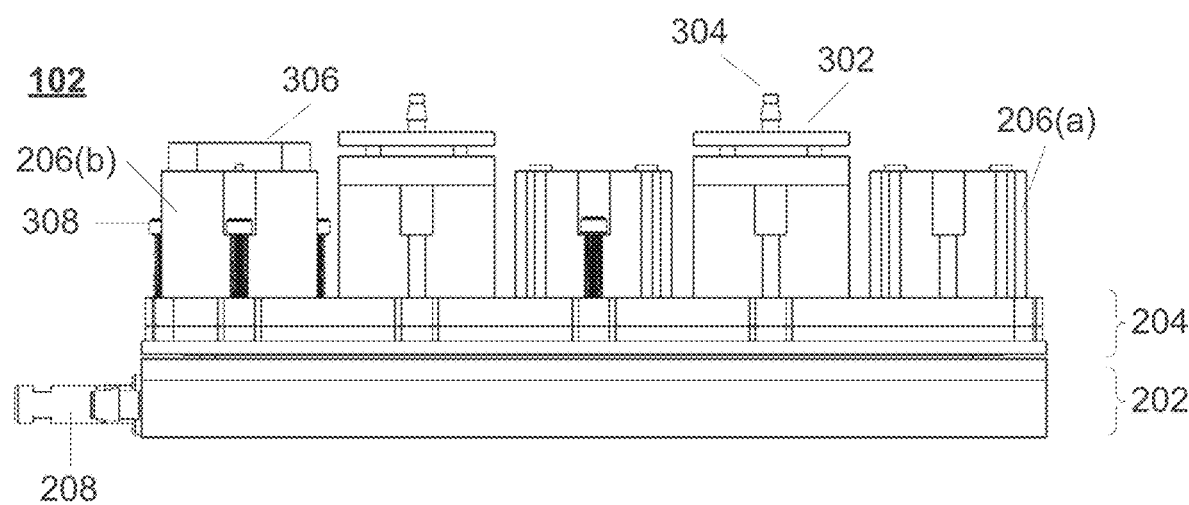

FIG. 3B is a side view of the model from FIG. 3A illustrating the cell culture platform 102. In some implementations, the cell culture vessels 206 are sealed with reversibly coupled lids 302 and 306. The lid 302 includes a port 304, which in some implementations, is used to flow gases and/or liquids into the cell culture vessel 206(b). The lid 306 is a sealed lid and does not include a port. As illustrated, the cell culture vessels 206 are coupled to the fluid flow plate 204 with screws 308.

Below, each of the control plate 202, the fluid flow plate 204, and the cell culture vessels 206 of FIGS. 2, 3A, and 3B are described in turn and in greater detail with reference to FIGS. 4-9.

As set forth above in reference to FIGS. 2, 3A, and 3B, the cell culture platform 102 includes a control plate 202. In general, the control plate 202 contains reusable connectors, actuators, and/or sensors that interface with the fluid flow plate 204 and/or cell culture vessels 206. In some implementations, the placement of the connectors, actuators and/or sensors in the reusable control plate 202, provides a cost savings as portions of the cell culture platform 102 that directly interact with cells can be disposed of after experimentation, while the more expensive components can be reused. As described below, in some implementations, the control plate 202 is manufactured from a plastic or a multi-layer printed circuit board.

In some implementations, the control plate 202 includes between 5 and 10, between 10 and 30, between 30 and 50, between 50 and 100, or between 100 and 200 actuators. The actuators are used to control fluid flow through the fluid flow plate 204 and/or cell culture vessel 206, and, in some implementations, are used as pumps. The actuators control fluid flow by activating valves within the control plate 202, fluid flow plate 204 and/or cell culture vessel 206. In implementations where the actuators are configured as pumps, they pump between about 100 nL and about 500 nL, between about 500 nL and 1000 nL, or between about 1000 nL and about 2000 nL/min of fluid through a channel. The flow induced by the actuator pumps can have a continuous, single shot, and/or reciprocating flow profile.

In some implementations, the pump is configured to inject a predetermined dosage of a toxin, test agent, medicaments (e.g., antibiotics, vaccines, biologics, and medical countermeasures), or any combination thereof into the fluid flow plate 204 and/or the cell culture vessel 206. For example, on a predetermined cycle (e.g., once per day, three times a day, once per hour, etc.) the pump-configured actuator may be configured to deliver an insulin dose to a cell culture vessel containing liver cells. In some implementations, a pump-configured actuator withdraws a predetermined fluid sample volume from the fluid flow plate 204 and/or the cell culture vessel 206. For example, the actuator may withdraw 100 nL from a cell culture vessel every hour, such that a medicament, analyte, or toxin, or other biologically relevant material concentration can be determined in the cell culture vessel.

In various implementations, the actuators are pneumatic actuators, electromagnetic actuators, valves, or a combination thereof. The mechanism of the actuator activation is described further in relation to FIG. 9A, and the mechanism of the actuator when acting as a pump to inject or withdraw fluid samples is described in relation to FIG. 9B. Briefly, the actuators include a membrane, which is driven by a piston. When activated, the actuator drives the piston and membrane into a channel placed above the actuator. The membrane shunts the flow of a fluid through the channel. In some implementations, pneumatic actuators are used because in some implementations, the activation of an electromagnetic actuator may induce heat or electromagnetic noise that may interfere with certain sensor applications such as transepithelial electrical resistance.

The actuators enable customized control of fluids through the cell culture platform 102. The use of a membrane in the actuator enables separation of biological liquids from the reusable components of the control plate 202. In some implementations, the flexible membrane used in the actuator (and/or pump structures) is manufactured from, but is not limited to, polyimide- and polyurethane-based materials. In some implementations, substantially the entire, or at least large portions of, the top surface of the control plate 202 is covered with the membrane.

In some implementations, the control plate 202 includes a fixed form factor that couples (or mates) with the cell culture vessel 206 and/or the fluid flow plate 204. As described below, fluid flow plate 204 and cell culture vessel 206 can be configured differently responsive to the needs an experiment. In these implementations, the standardized form factor of the control plate 202 enables the mixing and matching of other modular components to the control plate 202.

As introduced above, the control plate 202 includes one or more sensors 106 and/or sensor connections. For example, the control plate 202 can include flow meters, gas sensors, pH sensors, temperature sensors, transepithelial electrical resistance (TEER) sensors, or any combination thereof. In some implementations, the flow sensor is a thermal flow sensor. In certain implementations, the sensors 206 are mounted to polyimide substrates and separated from fluids by the above described membrane.

In implementations including sensor connections (or sensor expansion ports) the sensors 106 described herein are added to the control plate 202 based on the requirements of an experiment. For example, a researcher conducting a flow experiment may choose to only attach flow sensors to the control plate 202 and may forgo other sensors such as a ph sensor. In some implementations, removing sensors 106 by decoupling them the from the expansion ports, facilitates the reusability of the control plate 202 by enabling delicate components of the control plate 202 to be removed prior to sterilization of the control plate 202. In some implementations, the sensor expansion ports are input/output ports for the controller 112, and allow for the connection of custom sensors to the control plate 202.

In some implementations, the control plate 202 includes at least one heating element. The heating element is employed to maintain a configurable temperature within one or more of the cell culture vessels 206. In some implementations, use of a heating element and closed cell culture vessels 206 enable experiments to be conducted without an incubator 104, as a predetermined microcondition can be maintained within each cell culture vessel 206.

In yet other implementations, the control plate 202 includes an auxiliary agent delivery module. The module connects to the control plate and enables specific agent dosage to one or more of the cell culture vessels 206.

To further describe the control plate 202 discussed above, FIGS. 4A-4C illustrate example implementations of the control plate 202. A person of ordinary skill in the art will recognize that features of the various control plates described below may be applied to any of the other control plates described herein.

Figure 4A:
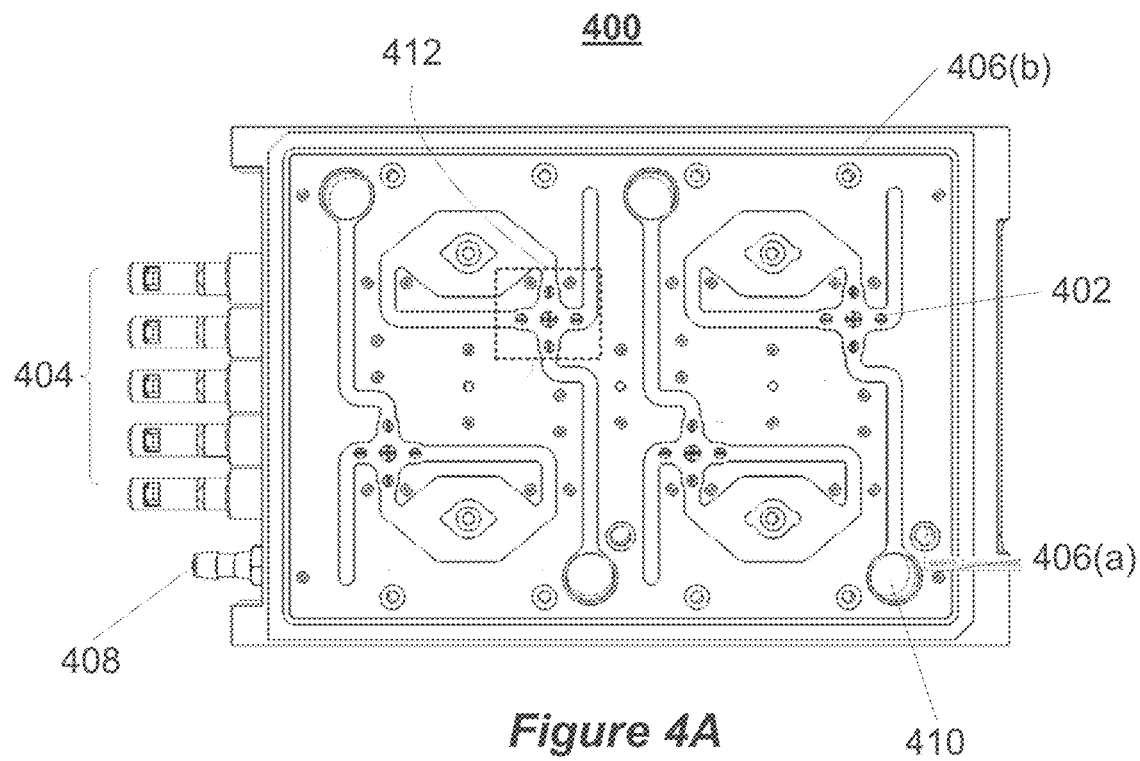
FIGS. 4A-4C illustrate solid models of example control plates that can be used in the cell culture system of FIG. 1.

FIG. 4A is a top view illustrating a pneumatic control plate 400. The control plate 400 includes a plurality of actuators 402 to act on flow channels within the fluid flow plate 204. The control plate 400 also includes a plurality of pneumatic ports 404 to control the plurality of actuators 402. A fluid flow enters the control plate 400 at inlet port 408 and exits the control plate 400 through the plurality of flow ports 406(*a*) and 406(*b*). The control plate 400 further includes a plurality of view ports 410 that provide optical access to the underside of the cell culture vessels 206.

As described above, the control plate 400 includes a plurality of pneumatic actuators 402. As illustrated, control plate 400 includes twenty actuators divided into four actuator groups 412. Each actuator group 412 corresponds to the intersection of two channels in the fluid flow plate 204. The actuator 402(*a*) lies at the center of the actuator group 412, and, when activated, stops the flow through all four branches of the intersection. Each actuator 402(*b*)-405(*e*) controls the flow of the fluid into its respective branch of the intersection.

The control plate 400 also includes a plurality of flow ports 406. As illustrated, the control plate 400 includes a first type of flow port, flow port 406(*a*), and a second type of flow port, flow port 406(*b*). Flow port 406(*b*) has a larger relative diameter compared to flow port 406(*a*). In some implementations, a larger diameter port 406 enables a greater relative volume of fluid to flow through the flow port 406. In some implementations, each flow port 406 is coupled to a single inlet port 408. In other implementations, the control plate 400 is configurable to provide separate sources to one or more of the flow ports 406. In some implementations, the opening of the flow port 406 is counter sunk into the control plate 400 and includes a washer or O-ring in the counter sunk area. The washer or O-ring prevents fluid leakage when a fluid flow passes from the control plate 400 to the fluid flow plate 204.

The control plate 400 also includes four viewing ports 410. The viewing ports 410 are pass throughs (or vias) that enable optical access to the dorsal side of the cell culture vessels 206 eventually coupled to the cell culture platform 102. In some implementations, the control plate 400, fluid flow plate 204, and/or cell culture vessels 206 are manufactured from optically clear materials such that cell cultures are optically accessible without view ports 410. In some implementations, the components of the cell culture system 100 are substantially optically clear and include a plurality of view ports 410.

Figure 4B:
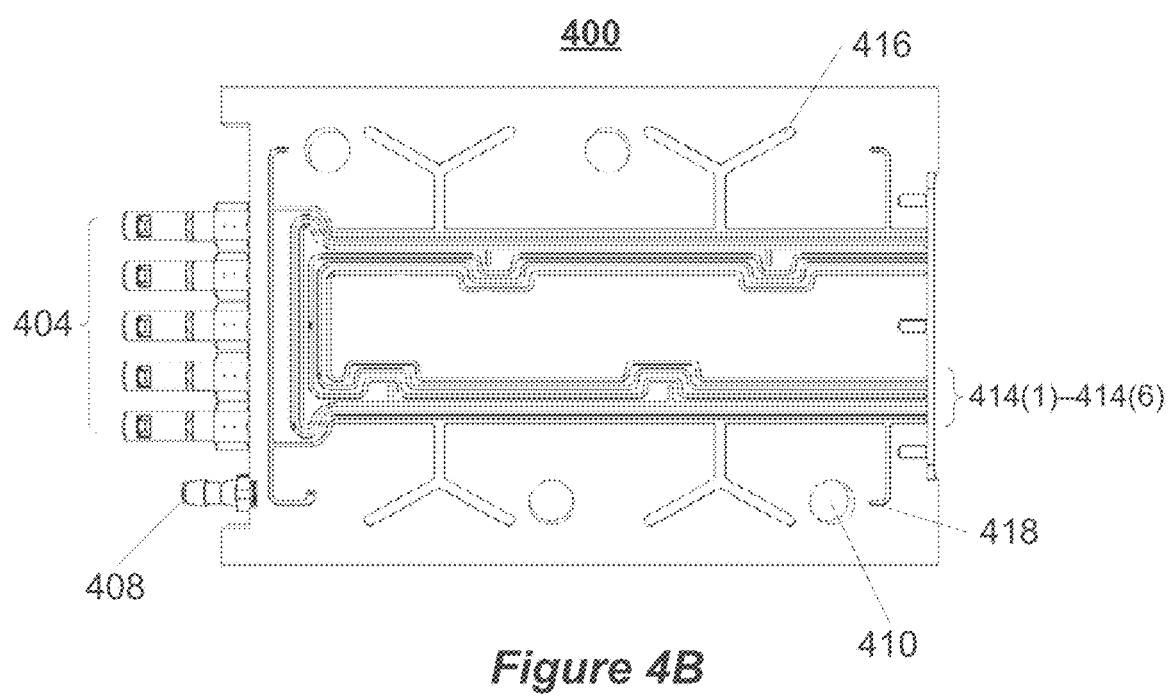

FIG. 4B is a cross sectional view illustrating the internal flow channels of the control plate 400. As illustrated, the control plate 400 includes the channels 414(1)-414(6). The channel 414(1) corresponds the fluid inlet port 408. The channels 414(2)-414(6) each correspond to one of the pneumatic ports 404 and act as control channels for the above described actuators 402(*a*)-402(*e*). FIG. 4B illustrates that each actuator group 412 is connected to the same control channels 414(2)-414(6), and thus operate in unison. In some implementations, each actuator 402 within actuator group 412 the control plate 202 is individually controllable.

The channel 412(1) includes a plurality of stems to route a fluid to the flow ports 406. The flow port 406(*b*) includes a relatively larger diameter compared to the flow port 406(*a*). Accordingly, stem 416, which corresponds to the larger flow port 406(*b*), includes a larger diameter to support the increased flow through flow port 406(*b*). In comparison, stem 418, which corresponds to flow port 406(*a*) includes a relatively smaller diameter. In some implementations, the stems 416 and 418 and the fluid flow channels described herein have a diameter of about 1-5 mm, about 5-10 mm, and about 15-25 mm.

Figure 4C:
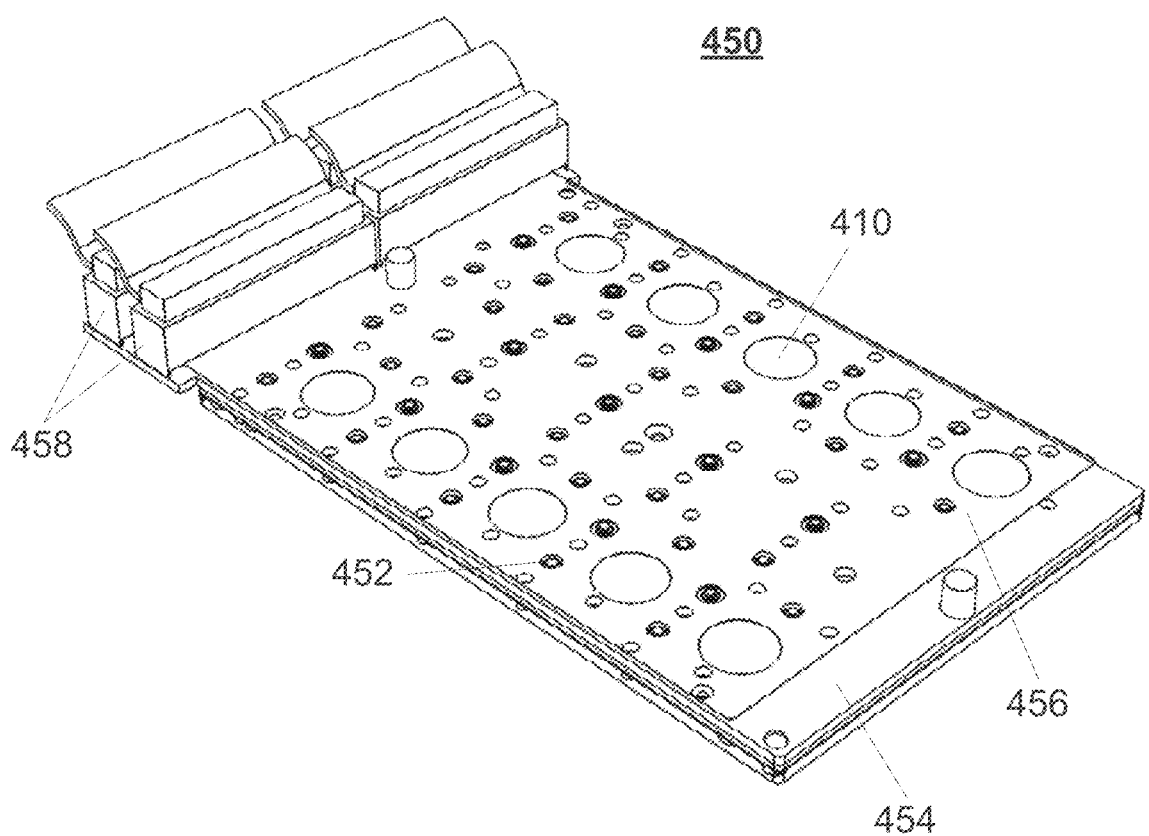

As described above, in some implementations, the actuator is an electromagnetic actuator. FIG. 4C is an isometric view of a control plate 450 with electromagnetic actuators 452. The control plate 450 is manufactured on a printed circuit board 454, and similar to control plate 400, includes a plurality of view ports 410. Additionally, the control plate 450 includes a membrane 456 that protects the electronics of the control plate 450 from the fluids contained in the above layers. The control plate 450 also includes a plurality of electrical connectors 458. As illustrated, control plate 450 does not include fluid flow channels. In this implementation, the fluid inlet port 408 would be included within the fluid flow plate 204 and/or cell culture vessels 206. In other implementations, the control plate 450 is configured to include a fluid inlet port 408 similar to control plate 400.

In some implementations, the electromagnetic actuators enable a smaller relative footprint compared to the control plate 400. In some implementations, the actuators 452 are implemented for bi-stable operation with fixed mechanical stops for the pistons they incorporate. This enables the actuators to have reproducible stroke volumes and only require power during engaged-unengaged transitions. As suggested above, in some implementations, the control plate 400 with pneumatic actuators is used when it is desired to have no, or a reduced number of, electrical components within the cell culture platform 102. For example, if an experimenter is performing electro-physiological experiments and the electrical components of the control plate 202 interfere with the electrophysiology recordings, then the experimenter may choose to use a pneumatic based system.

The control plate 450 also includes a plurality of connectors 458. In some implementations, the connectors 458 are used to electrically couple the control plate 450 to the controller 112 for the purpose of activating the actuators 452. In other implementations, the connectors 458 are used to connect sensors 106 to the control plate 450 and ultimately to the control computer 110. In some implementations, pneumatic implementations also include connectors 458 for the connection of sensors 106.

Referring back to FIGS. 2, 3A, and 3B, the cell culture platform 102 includes a fluid flow plate 204. The fluid flow plate 204 includes a plurality of flow channels defined therethrough. The fluid flow plate 204 acts as an interface between the control plate 202 and the cell culture vessels 206. For example, the fluid flow plate 204 interfaces on its dorsal side with the flow ports 406 of the control plate 400. A fluid flow is then routed from the control plate 202 to the fluid flow plate 204 where the fluid can be routed to the cell culture vessels 206.

In some implementations, the fluid flow plate 204 is constructed from transparent, chemically stable, and mechanically robust thermoplastic materials such as polystyrene. The material of the fluid flow plate 204 is selected to avoid chemical instabilities and chemical absorption.

In some implementations, dynamic control over flow through the fluid flow plate 204 is achieved using the above described actuators of the control plate 202. For example, the user can activate specific actuators to close, control the flow rate of, or route fluid away from channels.

In some implementations, the fluid flow plate 204 is disposable. In other implementations, the fluid flow plate 204 also includes actuators, sensors, and/or "reusable" components as described herein.

Figure 5A:
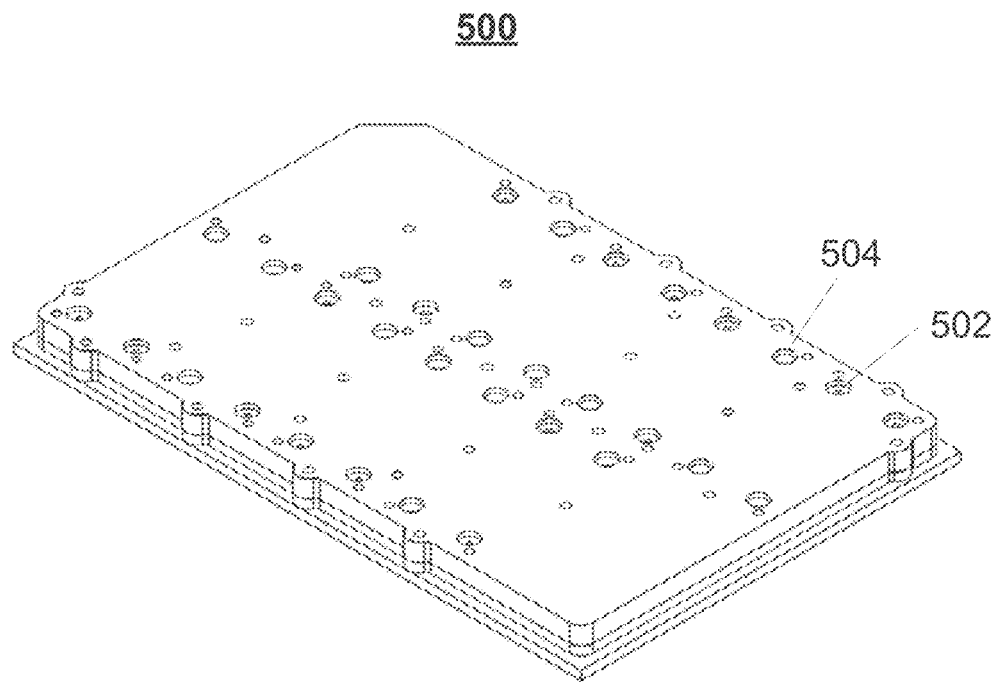
FIGS. 5A and 5B illustrate solid models of example fluid flow plates that can be used in the cell culture system of FIG. 1.

Now referring to FIG. 5A, which illustrates an isometric view of an example fluid flow plate 500. The top surface of the fluid flow plate 500 includes a plurality recesses (or mortises) 504. As described below, the cell culture vessels 206 include matching projections (or tenons). The mortises 504 and tenons interlock and properly align cell culture vessels 206 with the flow ports 502. As illustrated, the flow ports 502 are included in a subset of the mortises 504. In some implementations, each mortise 504 includes a flow port 502.

As illustrated, and referring back to FIGS. 3A and 3B, the fluid flow plate 500 supports six cell culture vessels 206. In some implementations, the fluid flow plate 500 supports between 1 and 10, 10 and 20, 20 and 50, 50 and 100 cell culture vessels 206.

Figure 5B:
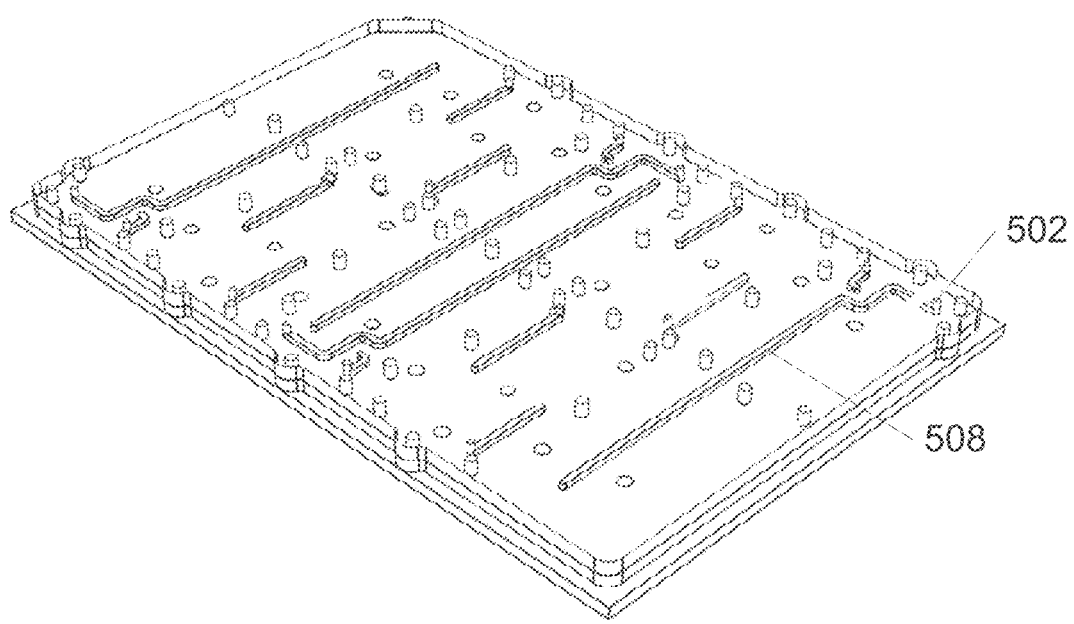

FIG. 5B illustrates a cross-sectional view of the fluid flow plate 500 from FIG. 5A. As revealed by the cross-sectional view, the fluid flow plate 500 includes a plurality of fluid flow channels 508. In some implementations, the fluid flow channels 508 connect one or more flow ports 502 to other fluid flow channels 508, flow ports 406 on the control plate 202, or a combination thereof. Thus, in some implementations, the fluid flow channels 508 connect one or more cell culture vessels 206, interconnect different portions of a single cell culture vessel 206, and/or connect the fluid flow channels 508 to the control plate 202. In some implementations, the fluid flow plate 500 includes a plurality of layers each of which include additional fluid flow channels 508. For example, the fluid flow plate 500 may include a first layer of fluid flow channels 508 that run along a first axis and a second set of fluid flow channels 508 that run orthogonal to the first axis.

Referring back to FIGS. 2, 3A, and 3B, the cell culture platform 102 includes a plurality of cell culture vessels 206(1)-(n), where n is the number of cell culture vessels. As described above, various cell culture platforms 102 can support between 1 and 10, between 10 and 20, between 20 and 50, or between 50 and 100 cell culture vessels 206. In some implementations, the cell culture vessels 206 are configured to house a specific cell type and/or cells from a particular organ type. In some implementations, the cells from the particular organ type include a plurality of cells types related to the particular organ. For example, when the cell culture vessel 206 is configured to house organ cells, the cell culture vessel can be configured to culture Loop of Henle thin segment cells, tubule cells, collecting duct cells, and glomerulus parietal cells. In some implementations with multiple cells types relating to a particular organ type, a first cell type related to the organ is cultured above a permeable membrane and a second cell type related to the organ is cultured below the permeable membrane.

In some implementations, the cell culture vessels 206 include a common exterior form factor regardless of the internal configuration of the cell culture vessel 206. For example, each cell culture vessel 206 can include the above described tenons and fluid ports at predetermined locations so the cell culture vessels 206 can be placed in any cell culture vessel slot on the fluid flow plate 202.

In some implementations, the cell culture vessels 206 are configured to support specific cell and/or organ tissue types. In some implementations, the cell culture vessels 206 may include specific scaffolds or structures to enable 3-dimensional cell growth of a specific cell and/or organ type. In other implementations, the cell culture vessels 206 are configured to support specific cell and/or organ tissue types by providing a predetermined flow rate to the cell culture vessel 206 and/or by providing predetermined fluids (e.g., specific media mixtures) to the cell culture vessel 206. For example, a cell type that requires a high shear force can be cultured in a cell culture vessel 206 with a plurality of input ports and a plurality of output ports. The plurality of input and output ports enable a relatively larger volume of fluid to flow through the cell culture vessel 206, thus imparting a relatively larger shear force on the cells within the cell culture vessel 206. In some implementations, cells that require little or no shear force may be cultured in cell culture vessels with a single port, such that nutrients diffuse into the cell culture vessel through the single port under no force from a fluid flow.

In other implementations, based on their physiological requirements, cells are cultured in a scaffold submerged in media or on a membrane at an air-liquid interface. For example, alveolar cells from the lung may be placed in a cell culture vessel 206 that is designed to provide air to the top-side of the cells while supplying the dorsal side of the cells with nutrients. In another example, liver cells may be cultured on a permeable membrane above a reservoir such that diffusion can occur through the liver cell layer and membrane to the reservoir.

As described in greater detail below, in some implementations, the cell culture vessels 206 include slots for one or more cell culture inserts. The cell culture inserts house the cells cultured in the cell culture vessel 206. The cell culture inserts are removable and enable the individual cultures to be seeded and grown outside of the cell culture system 100. For example, a company may sell pre-seeded cell culture inserts, which a researcher purchases and then inserts into a cell culture system 100.

In some implementations, the cell culture vessels 206 include multiple compartments that are separated by semi-permeable membranes. In some implementations, the membranes can include specific matrix components representing the surface chemistry, mechanical stiffness, and porosity of in vivo tissues. In some implementations, cells are cultured directly on the membranes.

As with the other components of the cell culture platform 102, in some implementations, the cell culture vessels 206 are disposable. The cell culture vessels 206 are manufactured from optically transparent materials such as polystyrene and/or polyimide. The cell culture vessels 206 materials are stable and compatible with cell culture and biological fluids relative to conventional microfluidic materials. For example, in some implementations, the cell culture vessels 206 are manufactured from PDMS. In some implementations, disposable cell culture vessel components are manufactured from thermoplastics such as polystyrene, polycarbonate, cyclic olefin copolymer (COC), or any combination thereof. In some implementations, the cell culture vessels 206 are manufactured by direct machining, embossing, injection molding, or any combination thereof may be used. In some implementations, the control plate 202 and/or fluid flow plate 204 are manufactured through similar processes with similar materials to those described above.

In some implementations, the cell culture vessels 206 and/or the fluid flow plate 204 include one-way valves. The one-way valves enable the cell culture vessels 206 to be temporally removed from the fluid flow plate 204 during experimentation. For example, a user may remove a cell culture vessel 206 from the cell culture platform 102 to perform a separate experiment or test on the cells within the removed cell culture vessel 206.

In some implementations, the above described fluid reservoir 118 and/or waste reservoir 120 can have the same form factor as a cell culture vessel 206, enabling the fluid reservoir 118 and/or the waste reservoir 120 to be modularly added to the cell culture platform 102. The fluid flow plate 202 and the control plate 202 can then flow growth media or other fluids (such as a medication or toxin) from the reservoir to the other components of the cell culture platform 102.

As described below, in some implementations, the cell culture vessels 206 include customized scaffold structures for each physiological system model. In some implementations, the scaffolds (also referred to as cell culture inserts) enable individual models to be developed separately from the cell culture platform 102 and then supplied individually for practical implementation.

In some implementations, specialized drug storage and delivery may be required for specific cell culture vessels 206 (e.g, delivering insulin to a cell culture vessel 206 culturing liver cells). These implementations can include custom modules fitted to the above described lids of specific culture wells. For example, and referring to FIG. 3B, the port 304 on lid 302 may be used to enable delivery of an agent to the interior of cell culture vessel 206(*b*). In some implementations, the delivery module is controlled by the control plate 202 and/or directly by the controller 112.

Figure 6:
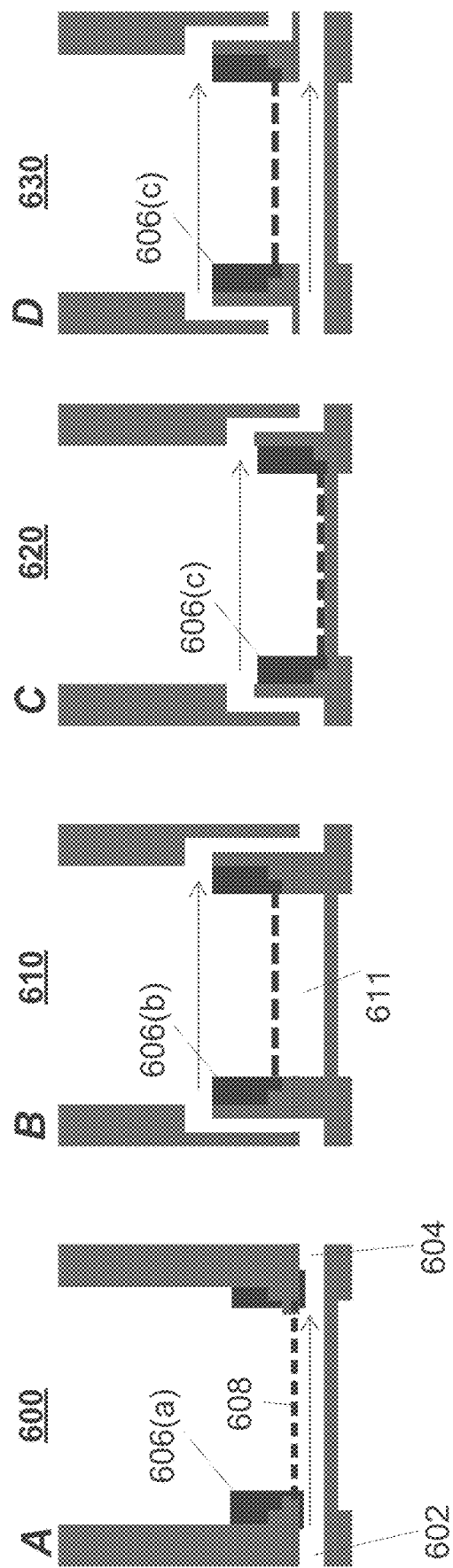
FIG. 6 illustrates example configurations of cell culture vessels that can be used in the cell culture system of FIG. 1.

FIG. 6 includes four panels, labeled A/D, which illustrate schematics of various example cell culture vessels 600, 610, 620, and 630. As illustrated, each cell culture vessel 600, 610, 620, and 630 includes an inlet port 602 and an outlet port 604. In some implementations, the cell culture vessels include a plurality of inlet ports 602 and/or a plurality of outlet ports 604. In certain implementations, each port of a cell culture vessel 206 is configured to be an inlet pot 602 or an outlet port 604 by configuring the fluid flow plate 204 with the one or more actuators in the control plate 202.

Each cell culture vessel 600, 610, 620, and 630 also includes a cell culture insert 606. As described above, the cell culture insert 606 enables the off-platform culturing of cells. The cell culture vessels include slots which secure the cell culture inserts 606 in place. In some implementations, the bottom surface of the cell culture insert includes a semi-permeable membrane on which cells are cultured.

Panel A of FIG. 6 illustrates a cell culture vessel 600 configured for a basal flow 608. As described above, some cells are responsive to specific flows and/or shear forces. For example, a cell population of liver cells may more closely mimic in vivo liver cells if exposed to a shear force. By employing a cell culture insert 606 with a permeable membrane, the configuration of cell culture vessel 600 exposes a cell's basal membrane to a flow and thus the described shear force. In some implementations, a basal flow allows the dorsal surface to be exposed to gases. For example, this type of configuration may be used to mimic alveolar tissue. In this example, alveolar epithelial cells are cultured in the cell culture insert 606. Nutrients are supplied to the cells through the basal flow 608, as the cells are exposed to gas along their top surface.

Panels B and C of FIG. 6 illustrate cell culture vessels 610 and 620, respectively. The cell culture vessels 610 and 620 are configured to provide a top flow. The cell culture vessel 610 includes a raised cell culture insert 606. The raised cell culture insert 606 enables diffusion through the cells and into a reservoir space 611 located beneath the insert 606(*b*). In some implementations, the cell culture configuration of cell culture vessel 620 is used to culture gut epithelial cells. Panel D of FIG. 6 illustrates the cell culture vessel 630. The cell culture vessel 630 is configured to allow flow above and below the cell culture insert 606.

Figure 7A:
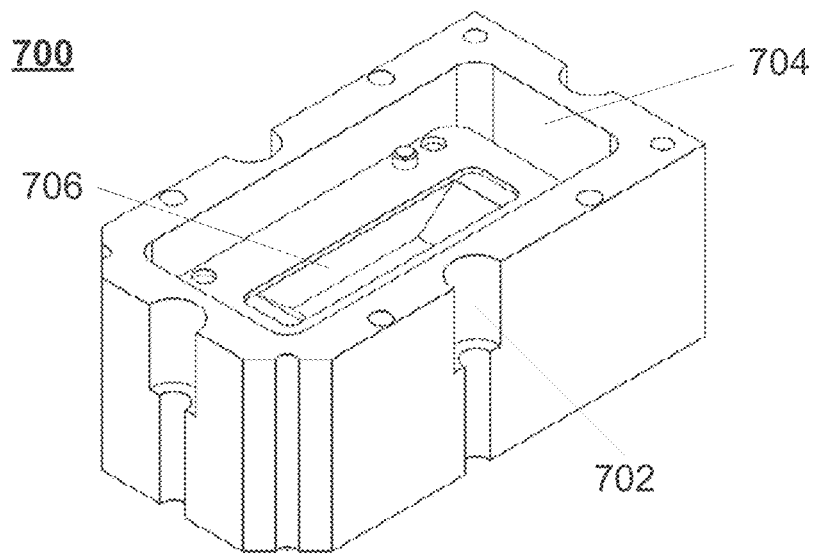
FIGS. 7A and 7B illustrate solid models of an example cell culture vessel.

FIG. 7A illustrates an isometric view of one example implementation of a cell culture vessel 630, similar to the cell culture vessel 206(*b*) in FIG. 3A. Exteriorly, each wall of the cell culture vessel 700 includes a recess used to secure the cell culture vessel 700 to a fluid flow plate 204 with thumb-screws. The interior of the cell culture vessel 700 includes a top flow area 704 and cell culture area 706. In some implementations, the floor of the cell culture area 704 is a semi-permeable membrane.

Figure 7B:
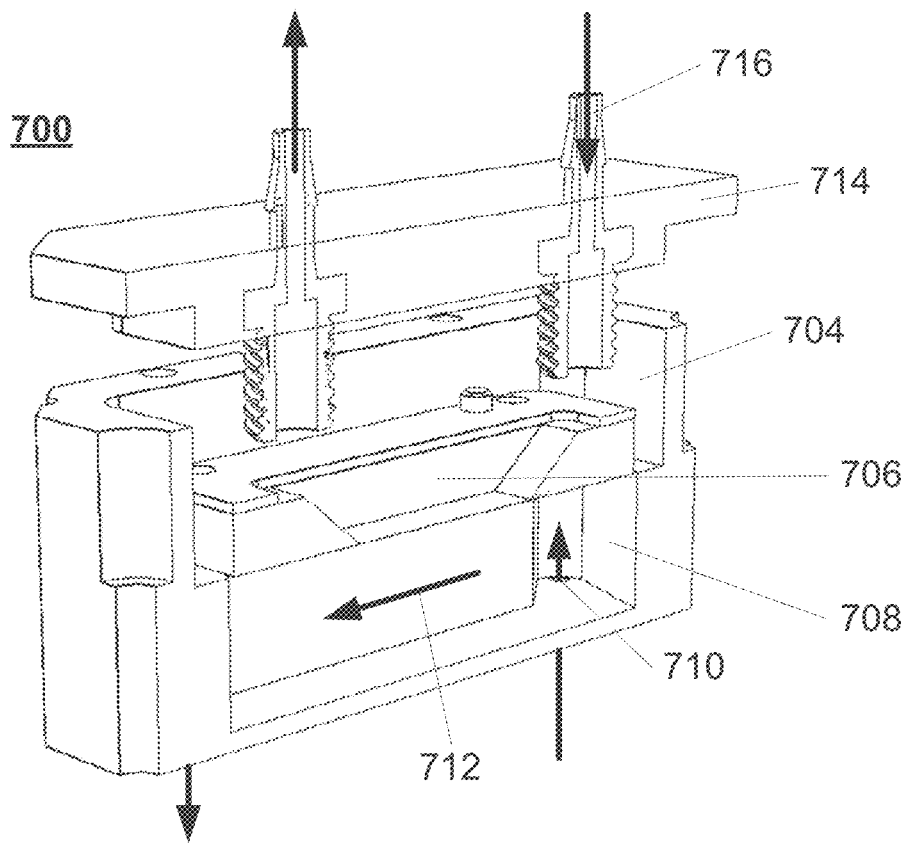

FIG. 7B illustrates an isometric cutaway view of the cell culture vessel 700. As revealed by the cut-a-way, the cell culture vessel 700 includes a lower flow area 708. Fluid flows into and out of the lower flow area 708 through ports 710. The arrow 712 illustrates one possible flow pattern through the cell culture vessel 700. A lid 714 is optionally coupled to the cell culture vessel 700. The lid 714 is manufactured with similar materials as the cell culture vessel 700. In some implementations, the lid 714 is transparent to provide optical access to the cells within the cell culture area 706. The lid 714 also includes a plurality of access ports 716. In some implementations, the access ports 716 are used to introduce a gas and/or a liquid into the top flow area 704. The gas and/or liquid is supplied to the access ports 716 through the control plate 202 and/or the fluid flow plate 204 in some implementations. In other implementations, the gas and/or liquid supply to the access ports 716 is independent of the cell culture platform 102. In some implementations, the cell culture vessel 700 is used to culture lung tissue. For example, lung cells are cultured within the cell culture area 706. Nutrients in the lower flow area diffuse to the cells through the semi-permeable membrane of the cell culture area 706. Gas, emulating gas within a human's lungs, is passed into the top flow area 704 through the access ports 716.

Figure 8:
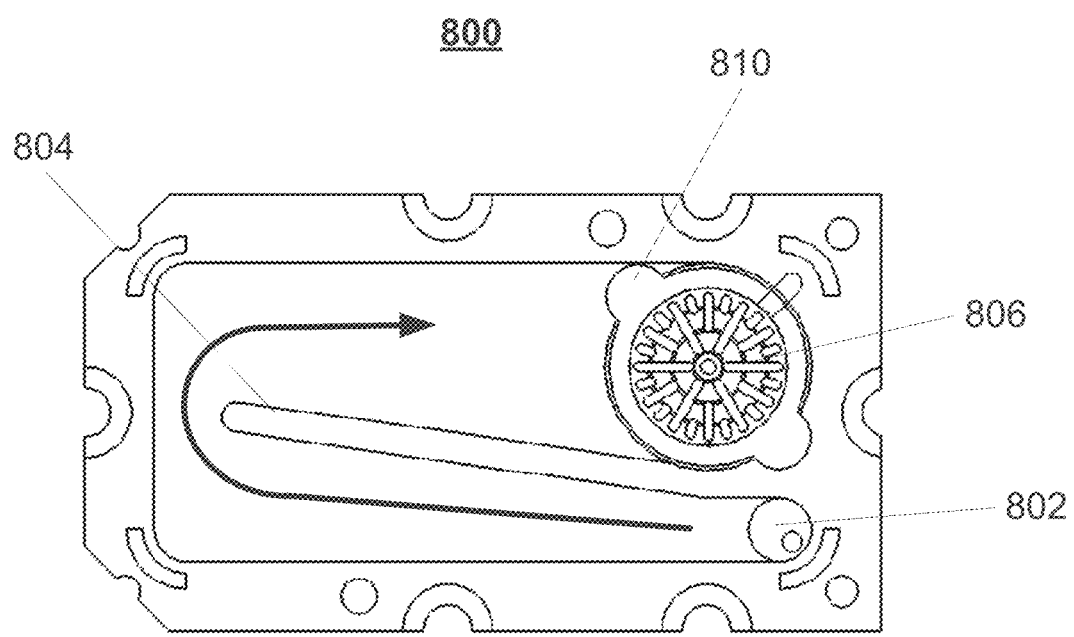
FIG. 8 illustrates a solid model of an example cell culture vessel.

FIG. 8 illustrates another implementation of a cell culture vessel 206. FIG. 8 illustrates a top view of cell culture vessel 800, similar to the cell culture vessel 206(*a*) in FIG. 3A. The cell culture vessel 800 includes an inlet port 802. The fluid flow entering the cell culture vessel 800 is directed around a wall 804 and toward an outlet 806. The outlet 806 is recessed within a slot 808, which is similar to above described slots for securing the cell culture inserts. In the cell culture vessel 800, a portion of the fluid flow flows through the cells and membrane of the cell culture insert to reach the outlet 806. Recesses 810 enable excess fluid to bypass the cell culture insert and flow directly to the outlet 806. In some implementations, a cell culture vessel similar to the cell culture vessel 800 is used for culturing cells, such as liver cells, in the presence of a shear force.

Figure 9A:
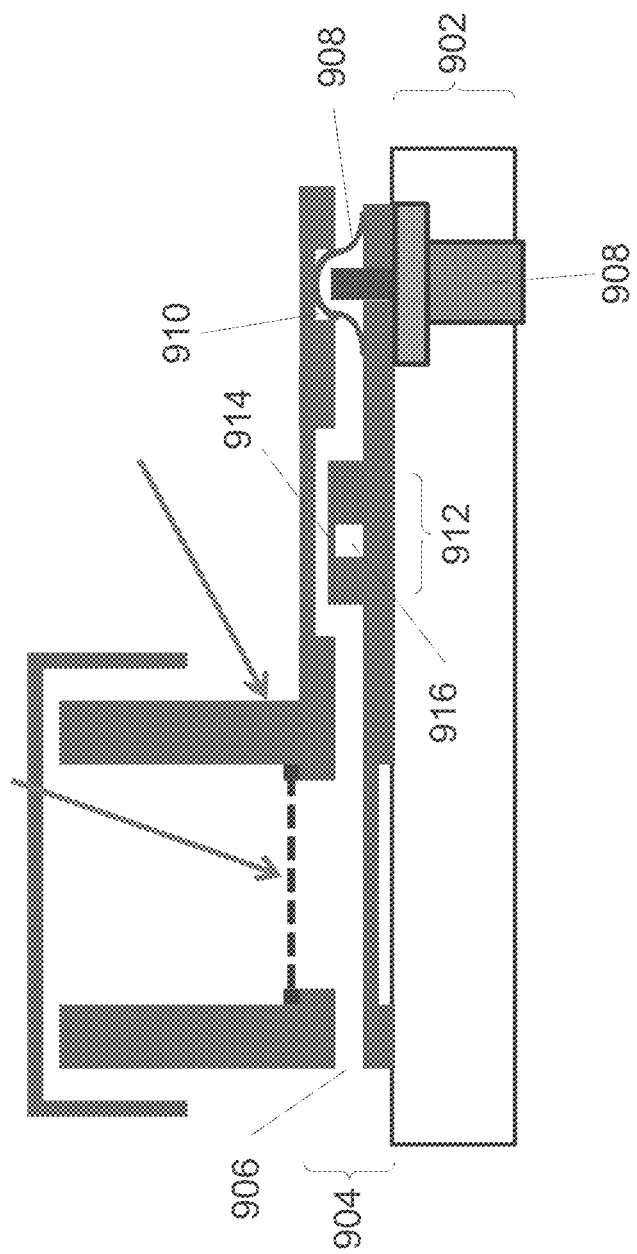
FIG. 9A illustrates a schematic of an example actuator that can be used in the cell culture system of FIG. 1.

FIG. 9A illustrates a cross sectional view of an actuator 900 suitable for inclusion in the control plate for controlling fluid paths in the fluid flow plate. The actuator 900 is housed within control plate 902. A fluid flow plate 904, which includes the flow channel 906, is coupled to the control plate 902. To close the flow channel 906, the actuator 900 drives its piston upward. As described above, a membrane 908 separates the actuator from the fluid of the fluid flow plate 904. Once deployed the piston drives into a recess 910 in the top of the flow channel. This creates a seal, closing the channel 906.

FIG. 9A also illustrates a fluidic capacitor 912. In some implementations, one or more fluidic capacitors 912 are included in the flow channels of the cell culture platform 102. The fluidic capacitor 912 smooths a fluid flow through the channel to which it is attached. The fluidic capacitor 912 includes a membrane 914 above a cavity 916. Responsive to a pulsatile wave (or other non-smooth flow) the membrane 914 deforms into the cavity 916. The expansion of the channel into the cavity 916 slows the pulsatile wave and smooths the flow through the channel.

Figure 9B:
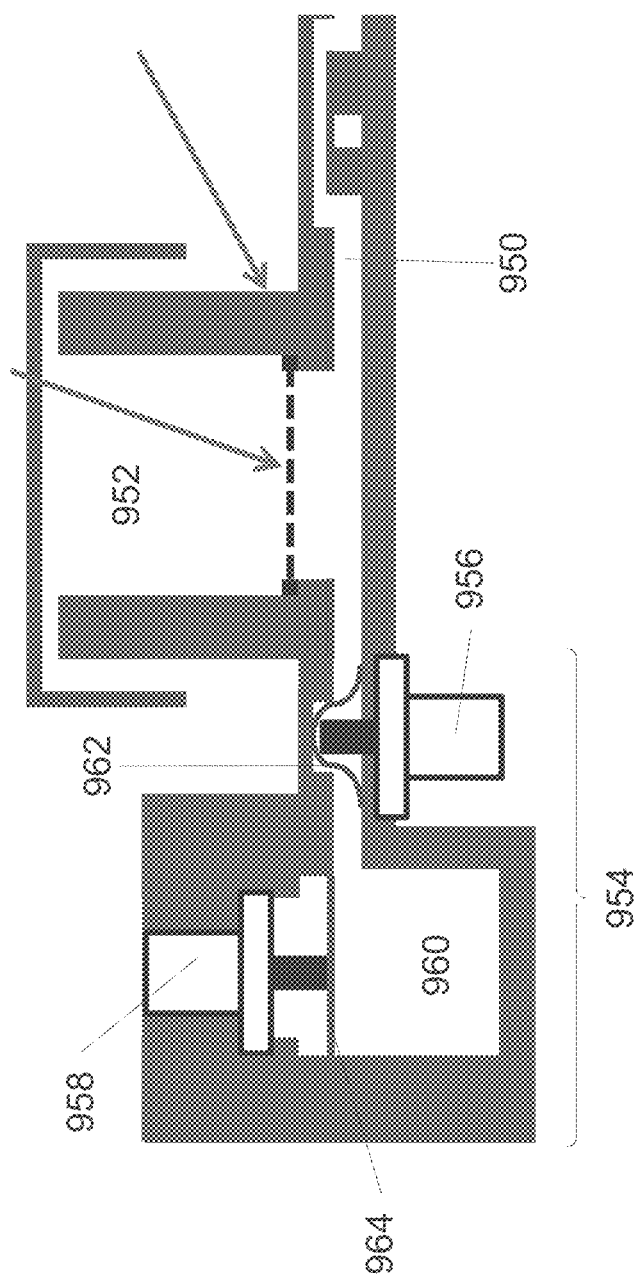
FIG. 9B illustrates a schematic of an example implementation of an actuator configured to inject and withdraw fluid samples that can be used in the cell culture system of FIG. 1.

FIG. 9B illustrates a cross sectional view of example actuators configured to inject and/or withdraw fluid samples for a cell culture system. As illustrated in FIG. 9B, a fluid channel 950 runs below a cell culture vessel 952. An injection/withdrawal (I/W) module 954 is coupled to one end of the channel 950. The I/W module 954 includes a first actuator 956, which when activated seals the I/W module 954 off from the fluid channel 950. The mechanism of the first actuator 956 is similar to the above described actuator 908 illustrated in FIG. 9A. Briefly, the first actuator 956 drives a membrane 962 into a recess in the top of the fluid channel 950, which creates a seal and closes the I/W module 954 off from the fluid channel 950. The I/W module 954 also includes a second actuator 958, which is coupled to a second membrane 964. The I/W module 954 also includes a reservoir 960 to store a fluids for injection and/or after withdrawal. In some implementations, the I/W module 954 also includes an access port (not illustrated) to enable the injection and/or withdrawal of fluid from the reservoir 960.

To withdraw (also referred to as sipping) a sample from the fluid channel 950, the first actuator 954 lowers. With the first actuator 954 lowered, a fluid can enter the I/W module 954. The second actuator 958 retracts its piston, and drives the second membrane 964 upward. The upward movement of the membrane 964 creates a vacuum in the reservoir 960, which draws a fluid from the fluid channel 950 into the reservoir 960. To inject a fluid into the fluid channel 950, a similar process occurs. During a fluid injection, the second actuator 958 extends its piston, creating a pressure build up in the reservoir 960. Responsive to the first actuator 956 opening access to the fluid channel 950, the pressure build up drives the fluid in the reservoir 960 out of the I/W module 954 and into the fluid channel 950.

In some implementations, the I/W module 954 does not require the second actuator 958 to withdraw fluid from the fluid channel 950. For example, the flow present in the fluid channel 950 may drive fluid into the reservoir 960. In some implementations, the I/W module 954 is a component of the above described fluid flow plate, cell culture vessels, or control plate. For example, the I/W module 954 may be a component of a cell culture vessel and inject or withdraw fluid directly from the cell culture vessel. In other implementations, the I/W module 954 is a separate module form the cell culture platform, and may be modularly added to any of the cell culture vessels and/or the fluid flow plate.

Figure 10:
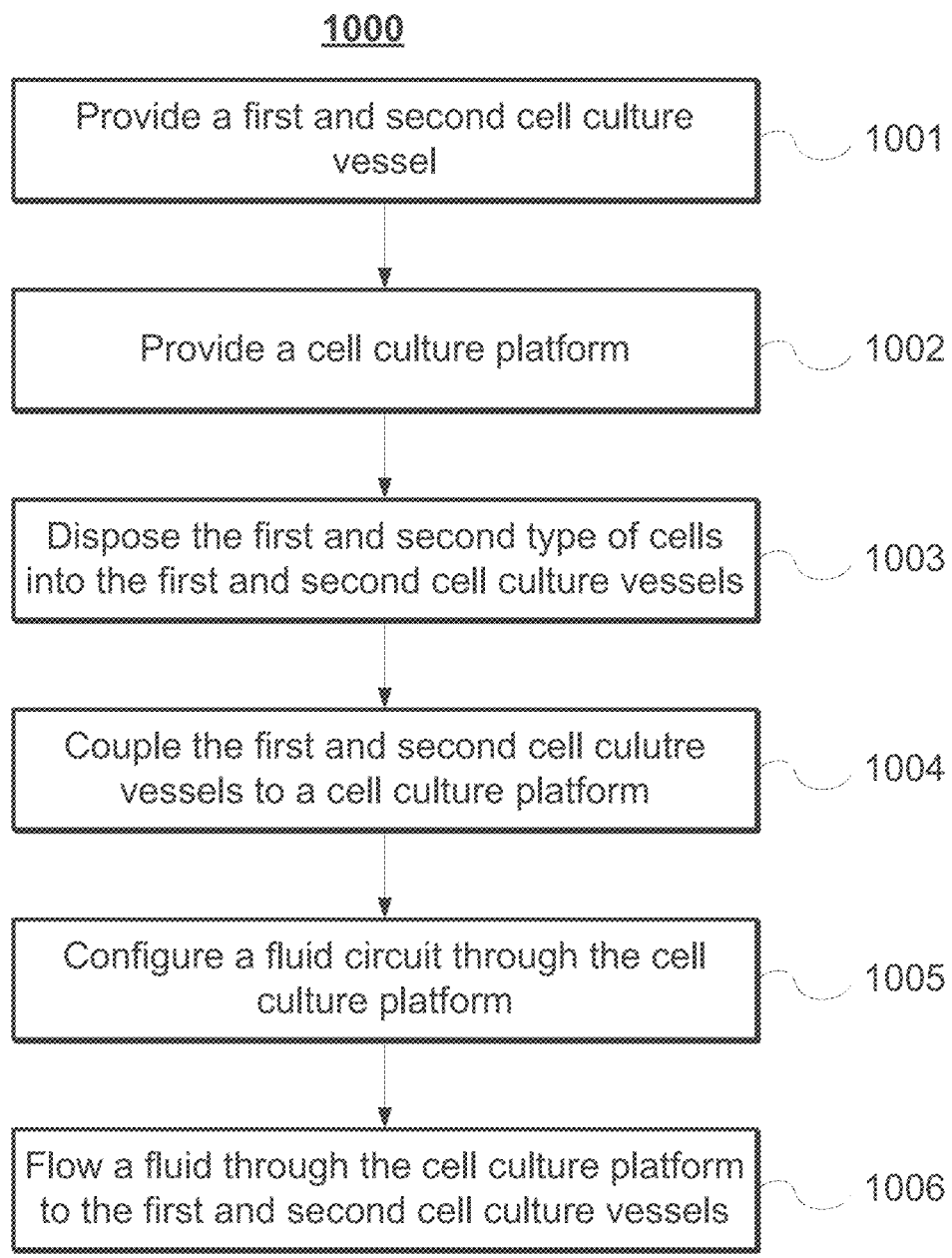
FIG. 10 illustrates a flow chart of an example method for culturing cells in the cell culture system of FIG. 1.

FIG. 10 illustrates a flow chart of a method 1000 for culturing a plurality of cells. In some implementations, the method 1000 is used to test the interplay of organ systems in vitro. The method 1000 includes providing a first and second cell culture vessel (step 1001). The method 1000 also includes providing a cell culture platform (step 1002). Cells of a first type are disposed in the first cell culture vessel and cells of a second type are disposed in the second cell culture vessel (step 1003). Then, the cell culture vessels are coupled to the cell culture platform (step 1004) and a fluid path (also referred to as a fluid circuit) is configured to the first and/or second cell culture vessels (step 1005). The method 1000 also includes flowing a fluid through the cell culture platform to the first and second cell culture vessels (step 1006).

As set forth above, the method 1000 begins with the provision of a first and second cell culture vessel (step 1001) and cell culture platform (step 1002). The first and second cell culture vessels can be similar to the cell culture vessels described above in relation to FIGS. 2-3B, and 6-8. In some implementations, the first and second cell culture vessels are configured differently. For example, the first cell culture vessel can be configured to culture tissue from a first organ (e.g., lung tissue), and the second cell culture vessel can be configured to culture tissue from a second organ (e.g., liver tissue). For example, the first cell culture vessel may be the cell culture vessel 700 illustrated in FIG. 7A and the second cell culture vessel may be the cell culture vessel 800 illustrated in FIG. 8. In some implementations, the cell culture platform is the cell culture platform 102 discussed above. In some implementations, one or more cell culture vessels are already coupled to the cell culture platform 102 prior to the beginning of the method 1000.

Next, a first type of cells are disposed in the first cell culture vessel and a second type of cells are disposed in the second cell culture vessel (step 1003). In some implementations, the cell culture vessel configurations selected in step 1001 is responsive to the type of cells a user intends to use in step 1003. In some implementations, a user is able to mimic an organ system by combining a specific cell type with a specific cell culture vessel configuration. For example, a user may select to combine alveolar cells with a cell culture vessel configuration that provides a liquid-gas interface (e.g, the cell culture vessel 700 illustrated in FIGS. 7A and 7B).

In some implementations, the first and second cell types are different cell types. In these implementations, a user may combine different cell types and cell culture vessel configurations to mimic a plurality of organ systems. In some implementations, the organ systems correspond to two or more of a liver, a lung, or a kidney. As described below, in some implementations the modular combination of multiple organ systems enables a user to study the interactions between those organ systems. In other implementations, a user can use a cell culture platform culturing a plurality of interconnected organ systems to study drug dosing and drug uptake.

Next, the first and second cell culture vessels are coupled to the cell culture platform (step 1004). In some implementations, as described above in relation to FIGS. 2-3B, the cell culture vessels are coupled to a fluid flow plate, which acts as an interface between a control plate and the cell culture vessels. In some implementations, the cell culture vessels are reversibly coupled to the control plate and/or fluid flow plate.

The method 1000 further includes configuring a fluid circuit between the first and second cell culture vessels (step 1005). As described above, in some implementations, an actuator is coupled to (or within the control plate). Activation of the actuator controls at least one valve in the fluid flow plate and/or cell culture vessels. By activating the one or more actuators in the cell culture platform, a user configures a fluidic circuit that routes the fluid flow between the first and second cell culture vessels.

Responsive to coupling the first and second cell culture vessels to the control plate, a fluid is flowed through the cell culture platform to the first and second cell culture vessels (step 1006). In some implementations, the fluid enters the cell culture platform at an interface with the control plate and/or the fluid flow plate. In yet other implementations, the fluid enters the cell culture platform through one or more of the cell culture vessels. In some implementations, flowing the fluid through the cell culture platform constitutes recirculating the fluid through the cell culture platform. In some implementations, the fluid is a growth medium, blood, a gas, or any combination thereof.

In some implementations, the method 1000 further includes disposing a third cell type into a third cell culture vessel and then coupling the third cell culture vessel to the cell culture platform in addition to or in place of the first and second cell culture vessels. In other implementations, the method 1000 also includes reconfiguring the fluid circuit created in step 1006 by activating one or more actuators. For example, by activating one or more of the actuators, the above described fluid circuit can be reconfigured to include the third cell culture vessel. In other implementations, the method 1000 includes rearranging and/or removing the first, second, and/or third cell culture vessels within the cell culture platform. In yet other implementations, the method 1000 includes measuring a parameter within the cell culture platform 102. For example, a temperature in one of the cell culture vessels and/or a flow rate through the fluid circuit may be measured. In some implementations, a cell culture vessel is temporally removed from the cell culture platform 102 to perform the measurement. In other implementations, a cell culture vessel is permanently removed and replaced with a cell culture vessel housing similar or different cells or organ tissue type.

One of ordinary skill in the art will recognize that in some implementations the above method steps of the method 1000 may be performed in a different order or one or more of the method steps may be omitted. For example in one implementation, the fluid circuit may be configured prior to the coupling of the cell culture vessels to the cell culture platform. In a similar example, a user may purchase a fluid flow plate that includes preconfigured fluid flow channels and therefore does not have to be configured once coupled to the cell culture platform.

Figure 11:
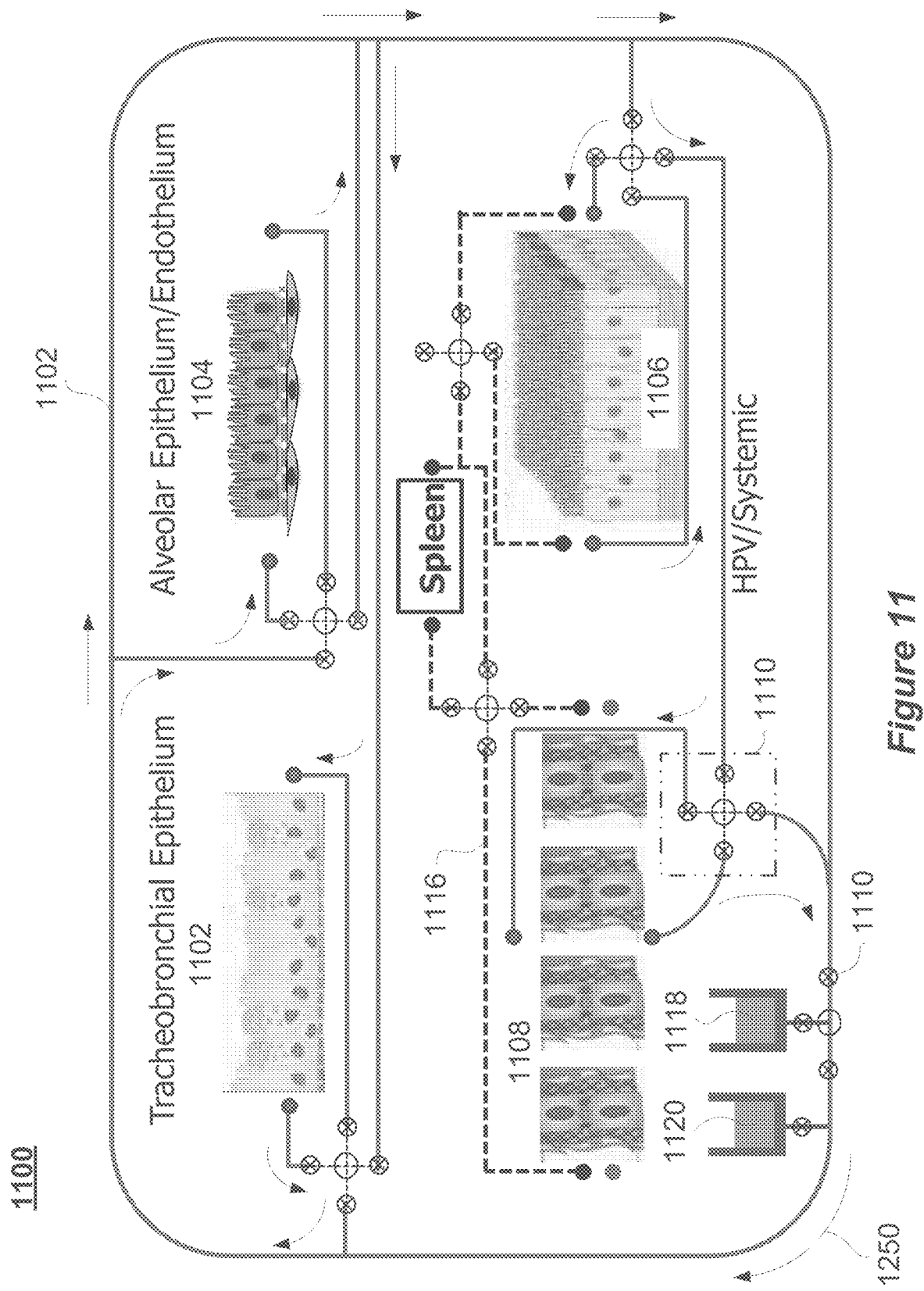
FIG. 11 illustrates a schematic of an example use case for the cell culture system of FIG. 1.

FIG. 11 illustrates an example schematic of a use case of the above described system. The schematic illustrates a system 1100 that, in some implementations, is used to investigate drug candidates. The system 1100 corresponds to a cell culture platform culturing cells that correspond to four organ systems. In some implementations, one or more cell culture vessels correspond to each organ system. The four organ systems of the system 1100 include tracheobronchial tissue 1102, alveolar tissue 1104, small intestine tissue 1106, and liver tissue 1108. Using the plurality of valves 1110 and valve groups 1112, which correspond to actuators in a control plate, two circulatory circuits are created within the fluid flow plate used to implement the system 1100. The first circuit 1114 represents a circulatory (or cardiovascular) system. The first circuit 1114 provides nutrients to each of the organ systems 1102, 1104, 1106, and 1108. In some implementations, the fluid used in the transport of nutrients and other chemicals to each of the organ systems 1102, 1104, 1106, and 1108 is a growth medium, blood, or a blood analyte. The second circuit 1116 (illustrated as a dashed line) is coupled to only the small intestine tissue 1106 and the liver tissue 1108. The second circuit 1116, small intestine tissue 1106, and liver tissue 1108 correspond to a lymphatic system and filter waste and other materials from the first circuit 1114.

In the system 1100, each of the cell culture vessels used to implement the system 1100, provide a top flow and a bottom flow, similar to the cell culture vessel 630 illustrated in Panel D of FIG. 6. For example, in the cell culture vessels corresponding to the alveolar tissue 1104 and the tracheobronchial tissue 1102, the cells are provided nutrients through fluid from the first circuit 1114, which flows through the lower chamber of the cell culture vessels. In the top chamber of the cell culture vessels, the alveolar tissue 1104 and the tracheobronchial tissue 1102 are exposed to oxygen. Exposure to oxygen on one side and the fluid of the first circuit 1114 on the other, enables the cells of the alveolar tissue 1104 and the tracheobronchial tissue 1102 to oxygenate the fluid while also removing $CO_2$.

The bottom flows in the cell culture vessels, which correspond to the small intestine tissue 1106 and the liver tissue 1108, also originate from the first circuit 1114. As described above, fluid from the first circuit 1114 is used to supply the respective tissue with nutrients. In the cell culture vessels that correspond to the small intestine tissue 1106 and the liver tissue 1108, the top flow is a component of the flow from the second circuit 1116. In addition to receiving nutrients from the fluid of the first circuit 1114, the small intestine tissue 1106 and the liver tissue 1108 filter the fluid of the first circuit 1114 and transfer the filtered waste to the fluid of the second circuit 1116, where it can be removed from the system 1100.

By culturing organ specific tissue types within a biomimetic environment (e.g., within a cell culture vessel as described above wherein the temperature, humidity, and other parameters mimic in vivo conditions) and interconnecting each of the organ systems in a physiologically meaningful way, experiments can be conducted on in vitro cells that substantially mimic the responses of in vivo cell populations. For example, a predetermined dose of a drug can be introduced to the system 1100 through the drug delivery system 1120. Starting at the drug delivery system 1120, the first circuit 1114 of the system 1100 transports the drug to each of the organ systems 1102, 1104, 1106, and 1108. The arrows 1250 illustrate the path taken by drug through the first circuit 1114. The cells uptake the drug as it flows through the first circuit 1114. Additionally, some of the drug is filtered out of the fluid of the first circuit 1114 as it circulates through the system 1100. For example, the alveolar tissue 1104 may remove some of the drug as an off gas when the alveolar cells remove $CO_2$ from the fluid of the first circuit 1114. The liver tissue 1108 may also filter the drug out of the fluid of the first circuit 1114 and then transfer the drug to the fluid of the second circuit 1116.

As the drug flows through the system 1100, a number of measurements can be made. For example, a user may monitor the pH of the fluid in the first circuit 1114 to determine if the drug is causing the fluid to become basic or acidic. A user may sample the waste collected in the fluid of the second circuit 1116 to determine if the drug dosage is too high. For example, a user may perform experiments wherein the drug dosage is lowered to the point where the drug is substantially not present in the fluid of the second circuit 1116. In some implementations, a substantial amount of drug in the fluid of the second circuit 1116 indicates that too much drug is being introduced into the system 1100.

In some implementations, the user may temporally remove one of the cell culture vessels corresponding to one of the tissue systems and examine the cells in the cell culture vessel with the above described microscope. For example, the user may examine the cells with a microscope to determine if the drug is causing damage to the cells. In some implementations, the user can examine cells within a cell culture vessel without removing the cell culture vessel from the cell culture platform.

The invention may be embodied in other specific forms without departing from the spirit or essential characteristics thereof. The forgoing implementations are therefore to be considered in all respects illustrative, rather than limiting of the invention.

What is claimed:

1. A system for culturing cells, comprising:
a disposable fluid routing plate including:
a planar upper mounting surface; a plurality of fluid channels; a plurality of locking and alignment recesses and flow ports extending within the planar upper mounting surface, each flow port being positioned relative to a separate corresponding subset of the locking and alignment recesses, the locking and alignment recesses configured for removably accepting mating locking and alignment features associated with respective individual first and second cell culture vessels for separately removably mounting the first and second cell culture vessels with mating surfaces on top of the planar upper mounting surface of the fluid routing plate at selected locations associated with selected flow ports, and properly aligning the first and second cell culture vessels with the selected flow ports, and for coupling the first and second cell culture vessels to selected respective channels of the plurality of fluid channels via the selected flow ports; and at least one valve coupled to at least two of the fluid channels configured to control a path of a fluid flow through the plurality of fluid channels to form a fluid path for respective first and second cell culture vessels; and
a reusable control plate configured for coupling to the fluid routing plate, including an actuator for controlling the at least one valve in the fluid routing plate.

2. The system of claim 1, further comprising the first and second cell culture vessels.

3. The system of claim 1, further comprising a processor coupled to the control plate and configured to output control signals to the control plate to configure the position of the actuator.

4. The system of claim 1, further comprising a sensor for measuring a parameter of a cell culture disposed in one of the first and second cell culture vessels.

5. The system of claim 4, further comprising a computer processor coupled to the sensor configured to receive data from the sensor to monitor the measured cell culture parameter.

6. The system of claim 1, wherein at least one of the receptacles is configured to receive a plurality of types of modular cell culture vessels configured for culturing different respective cell types.

7. The system of claim 1, further comprising a second actuator configured to introduce a predetermined amount of an agent into the plurality of fluid channels.

8. The system of claim 7, wherein the agent is one of a medication and a toxin.

9. The system of claim 1, further comprising a second actuator configured to withdraw a fluid sample from the plurality of fluid flow channels.

10. The system of claim 1, wherein the actuator is configured to control the state of the valve within the fluid routing plate to control flow rates of the fluid flow through the fluid routing plate.

11. The system of claim 10, wherein the actuator is configured to close the valve by deforming a control membrane within the valve, such that the membrane substantially impedes the flow of fluid through a channel in the fluid routing plate.

12. The system of claim 1, further comprising a fluid pump coupled to one of the control plate and the fluid routing plate to generate a fluid flow along the fluid path for respective first and second cell culture vessels.

13. The system of claim 1 in which the plurality of locking and alignment recesses and flow ports are of a quantity capable of accepting more than two cell culture vessels.

14. The system of claim 13 in which the locking and alignment recesses are mortises for engaging mating tenons.

15. The system of claim 13 in which more than 20 cell culture vessels are capable of being mounted on the planar upper mounting surface.

* * * * *